US012760261B2

(12) United States Patent
Marliere et al.

(10) Patent No.: US 12,760,261 B2
(45) Date of Patent: Oct. 13, 2026

(54) METHOD FOR THE ADAPTIVE EVOLUTION OF LIVING CELLS BY CONTINUOUS CELL CULTURE

(71) Applicant: Lesaffre et Compagnie, Paris (FR)

(72) Inventors: Philippe Marliere, Luxembourg (LU); Julien Patrouix, Villeneuve le Comte (FR); Simon Trancart, Saint Cloud (FR)

(73) Assignee: LESAFFRE ET COMPAGNIE, Paris (FR)

( * ) Notice: Subject to any disclaimer, the term of this patent is extended or adjusted under 35 U.S.C. 154(b) by 872 days.

(21) Appl. No.: 17/926,217

(22) PCT Filed: May 19, 2021

(86) PCT No.: PCT/EP2021/063352
§ 371 (c)(1),
(2) Date: Nov. 18, 2022

(87) PCT Pub. No.: WO2021/234033
PCT Pub. Date: Nov. 25, 2021

(65) Prior Publication Data

US 2023/0183630 A1 Jun. 15, 2023

(30) Foreign Application Priority Data

May 21, 2020 (FR) ....................................... 2005430

(51) Int. Cl.

| | |
|---|---|
| ***C12M 1/00*** | (2006.01) |
| ***C12M 1/42*** | (2006.01) |
| ***C12M 3/00*** | (2006.01) |
| ***C12M 3/06*** | (2006.01) |

(52) U.S. Cl.
CPC ............ *C12M 35/00* (2013.01); *C12M 23/58* (2013.01); *C12M 27/16* (2013.01); *C12M 29/24* (2013.01)

(58) Field of Classification Search
CPC .............................. C12M 35/00; C12M 23/58
See application file for complete search history.

(56) References Cited

U.S. PATENT DOCUMENTS

| | | | | |
|---|---|---|---|---|
| 2019/0085324 A1* | 3/2019 | Regev | ...................... | G16B 5/00 |
| 2020/0199568 A1* | 6/2020 | Bashor | ..................... | C12N 1/18 |
| 2022/0205001 A1* | 6/2022 | Rombouts | ................ | C12N 1/20 |

FOREIGN PATENT DOCUMENTS

| | | | | |
|---|---|---|---|---|
| CN | 108251299 A | 7/2018 | | |
| EP | 1135460 A1 | 9/2001 | | |
| WO | WO 2009/112739 A1 | 9/2009 | | |
| WO | WO 2018/122542 A1 | 7/2018 | | |
| WO | WO 2018/152442 A1 | 8/2018 | | |
| WO | WO-2020009017 A1 * | 1/2020 | ............ | C12M 41/48 |
| WO | WO-2020102562 A1 * | 5/2020 | ............ | C12M 35/00 |

OTHER PUBLICATIONS

International Search Report and Written Opinion for Application No. PCT/EP2021/063352, mailed Aug. 23, 2021.

(Continued)

*Primary Examiner* — Nathan A Bowers
(74) *Attorney, Agent, or Firm* — Maier & Maier, PLLC

(57) ABSTRACT

The present application relates to a method for adaptive evolution of living cells by continuous culture of said living cells.

20 Claims, 7 Drawing Sheets

(56) References Cited

OTHER PUBLICATIONS

International Preliminary Report on Patentability for Application No. PCT/EP2021/063352, mailed Dec. 1, 2022.
Mans et al., Under pressure: evolutionary engineering of yeast strains for improved performance in fuels and chemicals production. Curr Opin Biotechnol. Apr. 2018;50:47-56. doi: 10.1016/j.copbio.2017.10.011. Epub Nov. 20, 2017.
Sandberg et al., The emergence of adaptive laboratory evolution as an efficient tool for biological discovery and industrial biotechnology. Metab Eng. Dec. 2019;56:1-16. doi: 10.1016/j.ymben.2019.08.004. Epub Aug. 8, 2019.

* cited by examiner

[Fig.1a]
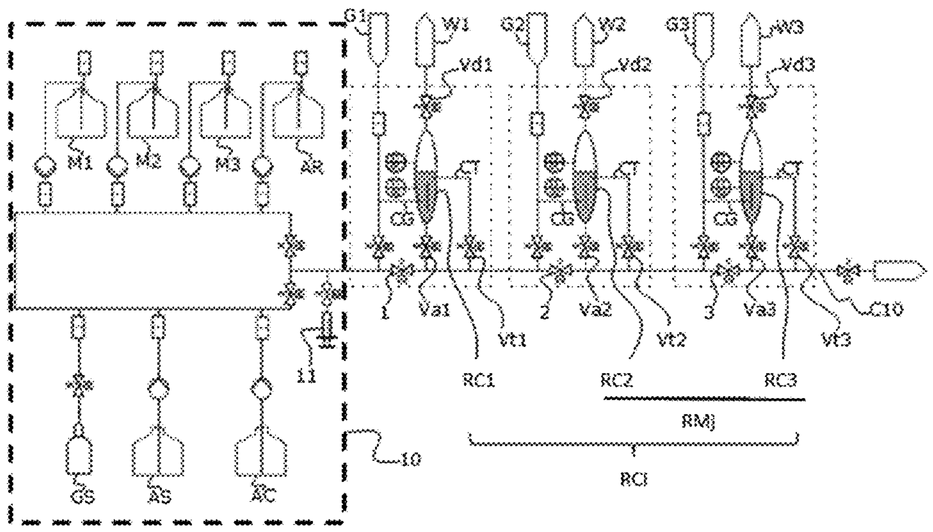
[Fig.1b]
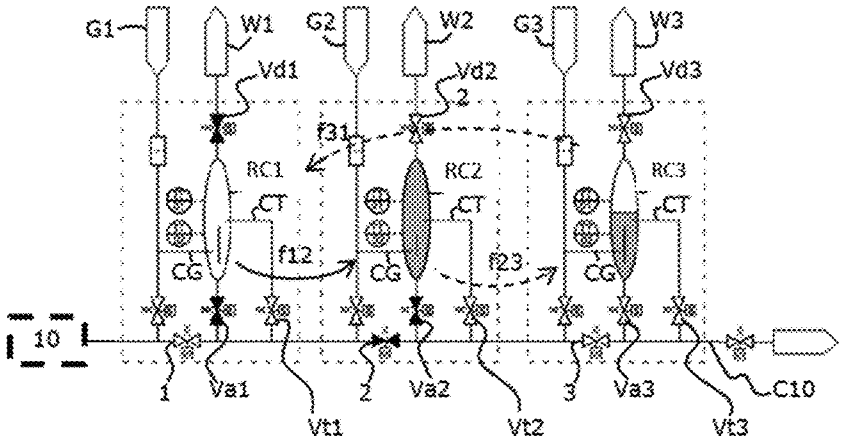
[Fig.1c]
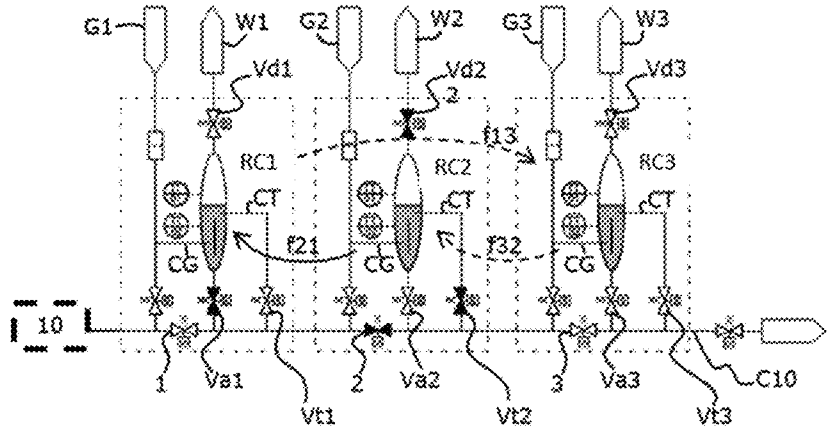

[Fig.2a]
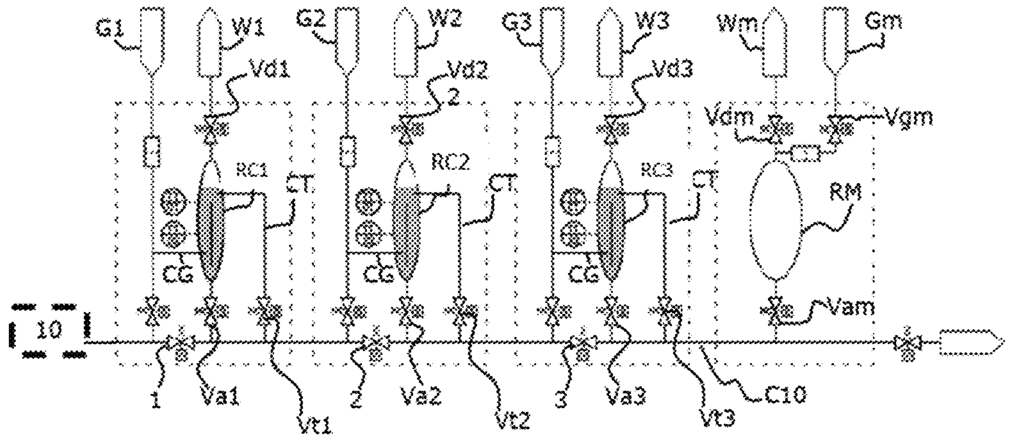
[Fig.2b]
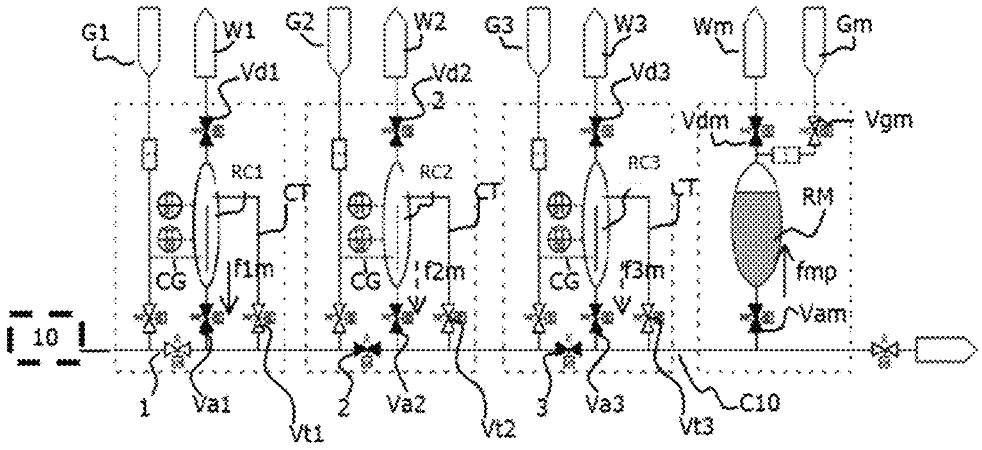
[Fig.2c]
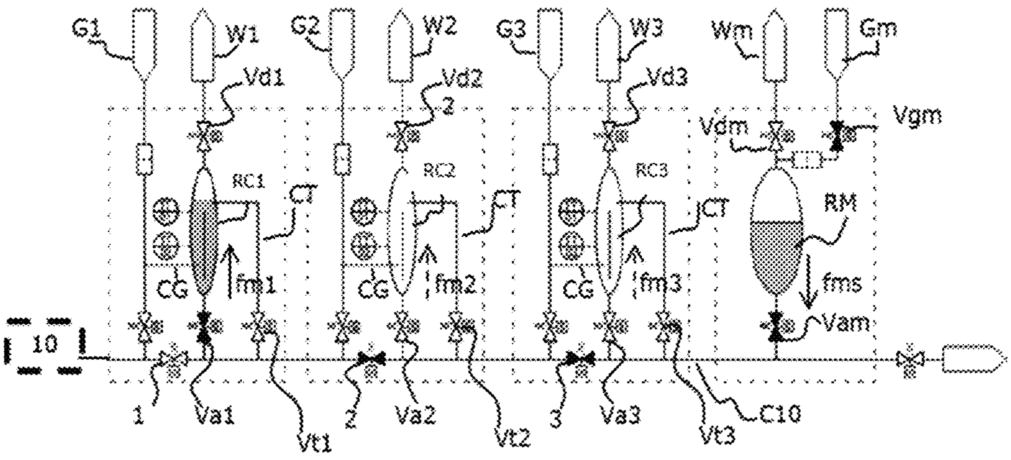

[Fig.3]
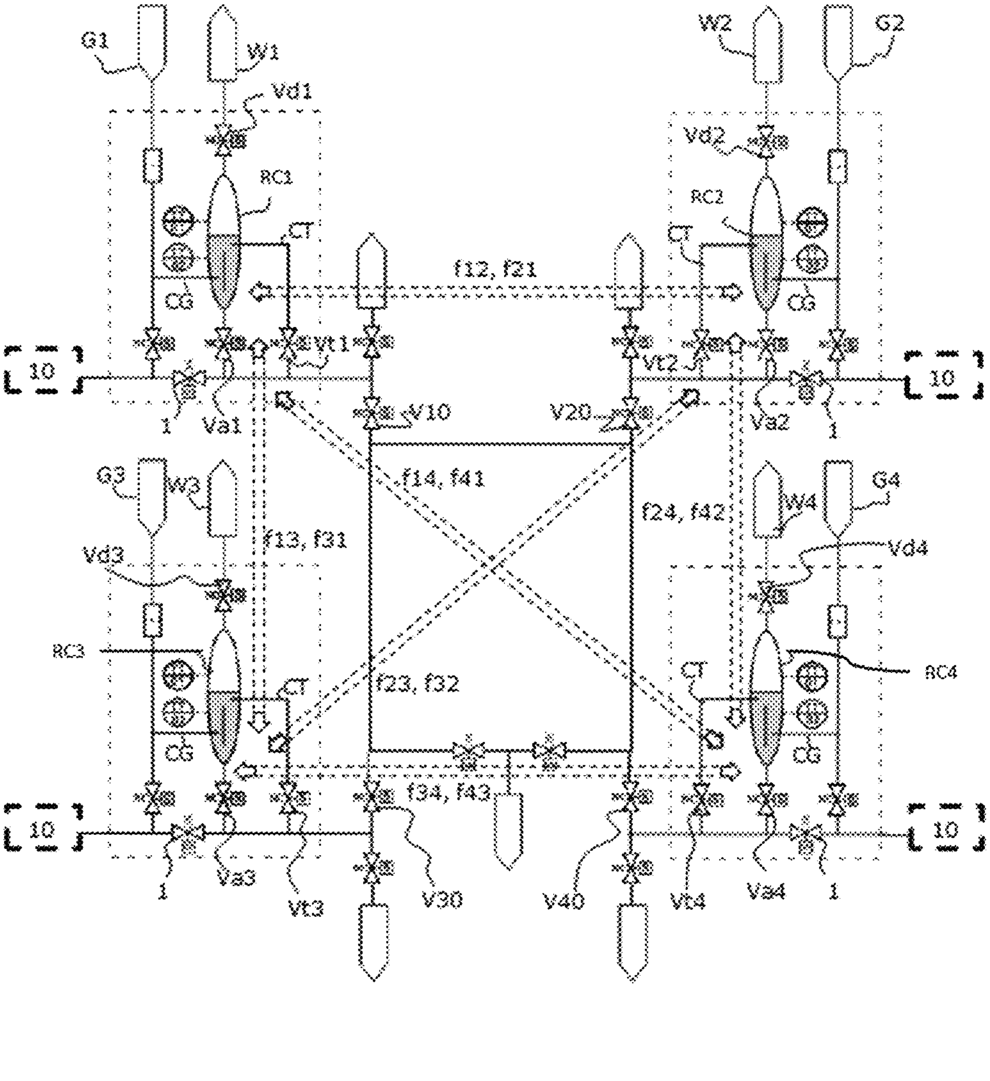

[Fig.4]
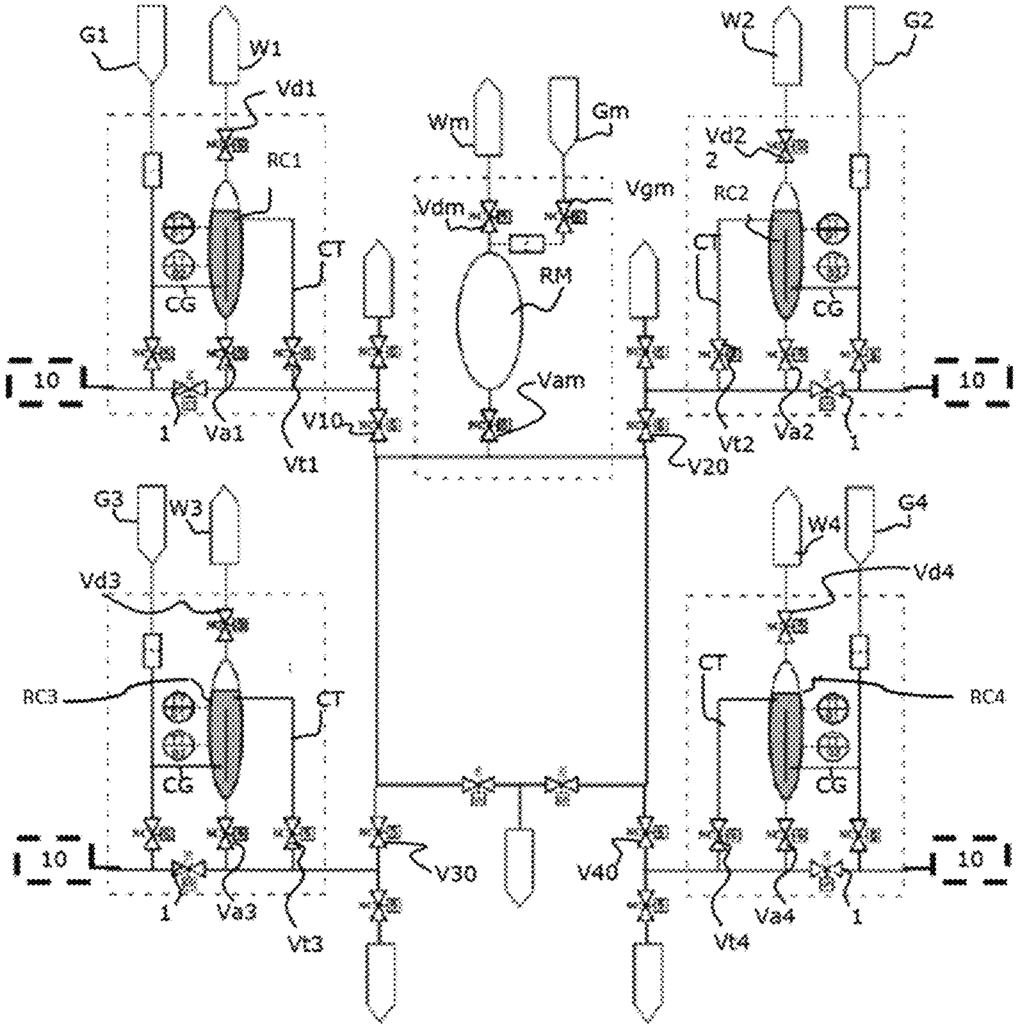

[Fig.5]
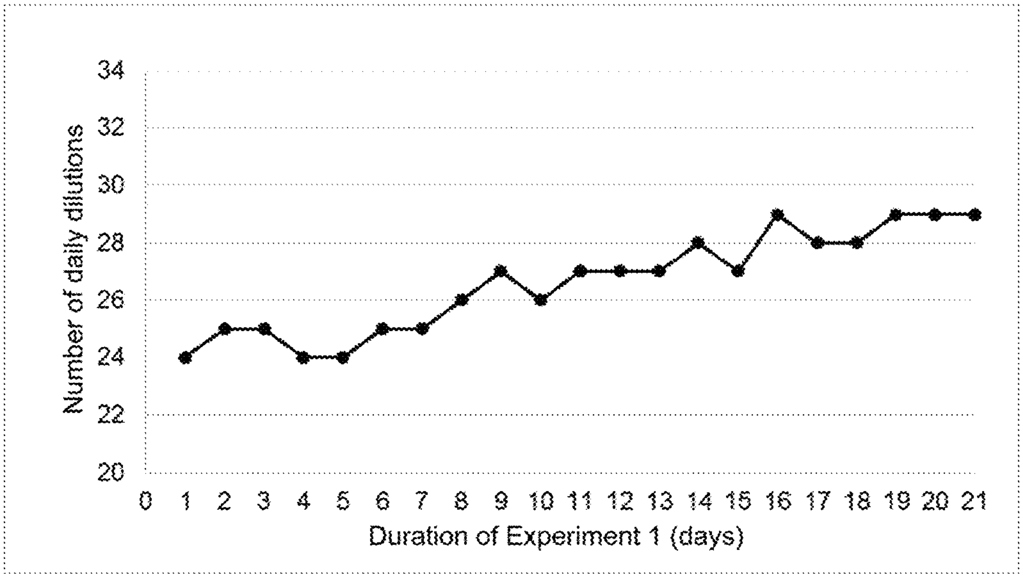
[Fig.6]
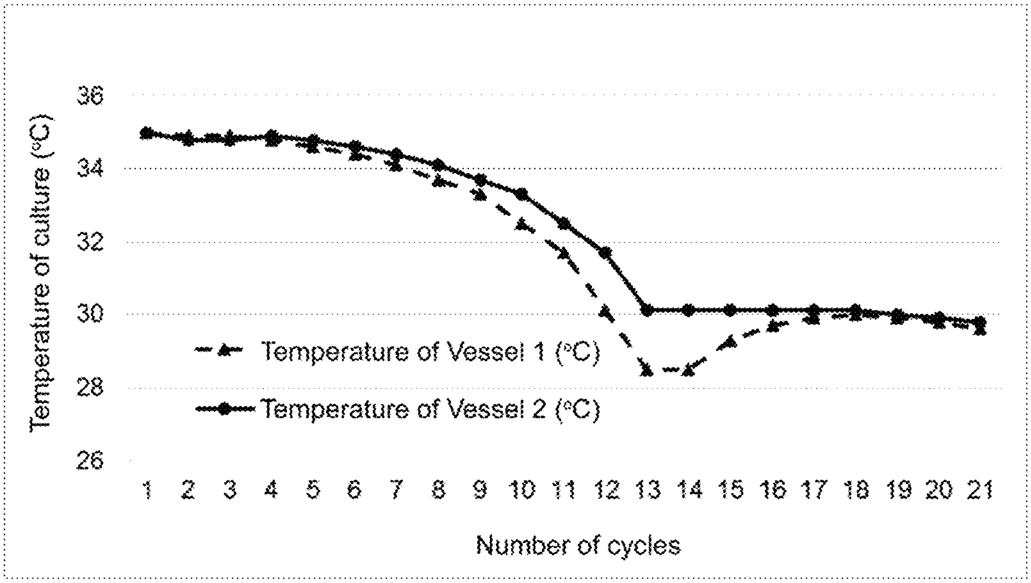

[Fig.7]
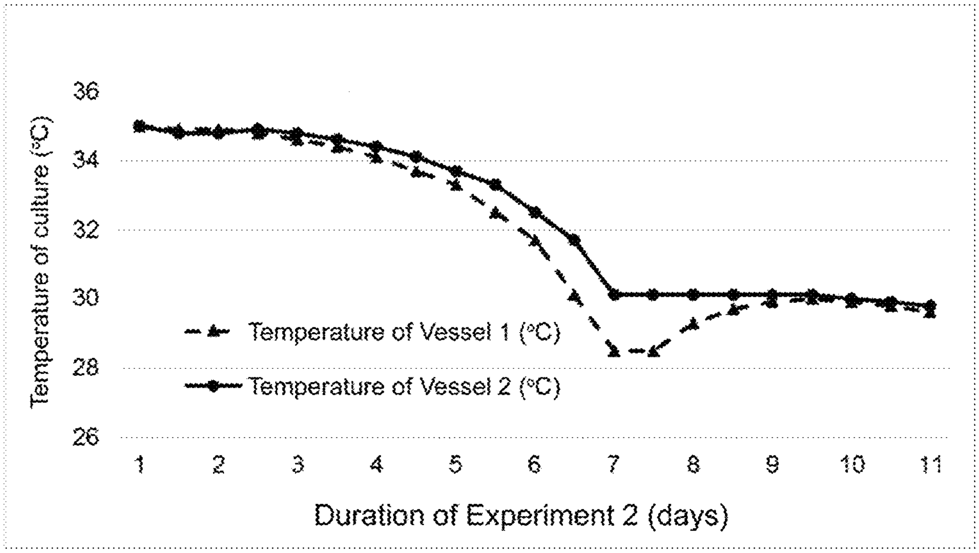
[Fig.8]
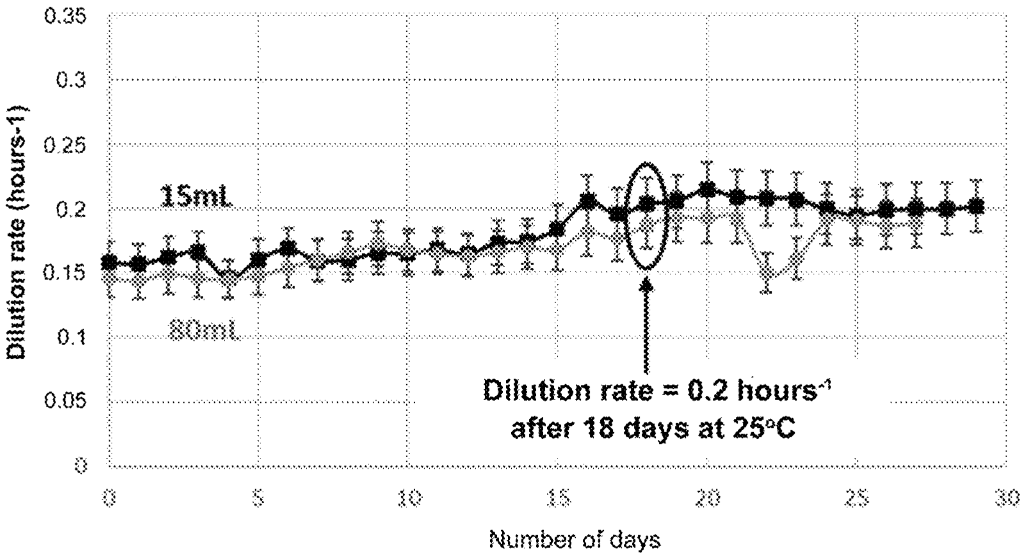

[Fig.9]
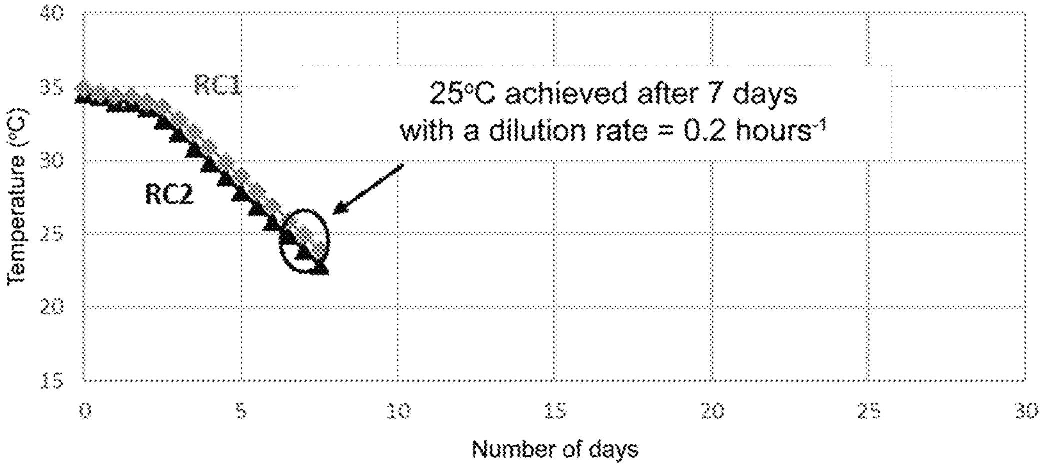

METHOD FOR THE ADAPTIVE EVOLUTION OF LIVING CELLS BY CONTINUOUS CELL CULTURE

RELATED APPLICATIONS

This application is a national stage filing under 35 U.S.C. § 371 of international application number PCT/EP2021/063352, filed May 19, 2021, which claims the benefit of French application number FR2005430, filed May 21, 2020, the contents of each of which are herein incorporated by reference in their entirety.

TECHNICAL FIELD

The present application relates to a method for adaptive evolution of living cells by continuous culture of said living cells.

PRIOR ART

Living cells are often used to produce, for example, foods, animal feed, flavors, cosmetics, fuels, chemicals, and health products. Living cells such as microalgae, fungi, yeast and bacteria have several advantages, including small cell sizes, short generation times and relatively low culture costs. However, the conditions required for efficient production of the product often differ from the optimal conditions for the growth and survival of said cell used in the industrial process.

The manufacture, degradation, or recycling of products requires high-performance living cells obtained under artificial conditions, which represent a compromise between the needs of the living cell and the conditions required to produce the product. To improve the desired performance of living cells, different approaches exist, including approaches involving genetic modification. However, several objections have been raised regarding genetically modified living cells and their uses, including in terms of safety and impact on other organisms, including humans. On the other hand, there is no model today that can completely predict which genetic modifications to apply to obtain a living cell with the desired phenotype.

Thus, alternative approaches are increasingly attractive. Such alternative approaches are for example based on the improvement of non-genetically-modified living cells by exploiting the potential of genetic variation occurring naturally in a population of microorganisms in order to generate mutants of industrial interest without knowledge of the mutations required to achieve the desired phenotype, while following the regulations prohibiting the use of genetically modified organisms.

Genetic variation is constantly generated, for example by random mutation and sexual reproduction. Therefore, living cells in a population vary in their level of adaptation to a given environment, which is the basis for selection. Selection refers to the tendency of beneficial phenotypic traits to increase in a given population of cells over time, as beneficial phenotypic traits improve the chances of survival, mating and/or reproduction of said cells. At the same time, phenotypic traits that reduce the chances of survival, mating and/or reproduction of said cells are reduced in frequency or even eliminated from the population. Thus, even under changing environments, populations can adapt to the respective environment based on the genetic variation present in the population by accumulating favorable, that is beneficial, phenotypic traits and eliminating deleterious, that is phenotypic traits with negative effects, over time. The potential for genetic variation is used, for example, in the context of artificial selection by selecting desirable phenotypic traits for the intended use such as efficient and commercially viable production of a product. However, effective artificial selection is difficult to implement.

Artificial selection faces the major challenge of choosing the best parameter(s) for selection pressure to effectively achieve a target phenotype, especially since too much selection pressure may limit the genetic diversity that can emerge through spontaneous mutations. Furthermore, in most cases, a selection of several phenotypic traits is required, such as phenotypic traits involved in improving growth rate, adaptation to a growth medium of different composition compared to a reference medium, adaptation to temperature, adaptation to an inhibitor present in a certain concentration and/or nutrient content. The selection of several phenotypic traits in a sequential manner, that is the improvement of phenotypic traits one after the other, imposes to go through intermediaries specialized on certain phenotypic traits from which the artificial selection to the other traits is difficult, tedious or even impossible. The improvement, by artificial selection, of several phenotypic traits in parallel, that is simultaneously, makes it possible to overcome this obstacle.

There is a need for alternative solutions to efficiently and automatically select living cells in suspension that have acquired a phenotype of interest, that is several traits simultaneously, under conditions optimized for low-cost and/or high-yield industrial production.

Patent application US 2012/0263690 describes a method for artificially selecting microorganisms that have acquired a single phenotypic trait selected from, among others, tolerance to temperature, tolerance to a chemical agent, and tolerance to ultraviolet radiation.

International application WO2009/112739 describes a method for selecting transiently enzyme-secreting suspension-growing cells of interest, said cells being maintained at a cell density value known to be a determinant of the secretion of the enzyme of interest.

Patent EP1135460 describes a method wherein cells are grown in a single selective regime, the chemostat or turbidostat.

The publication of Mans et al. (Mans et al, Current Opinion in Biotechnology, 2018, vol 50, pages 47-56) describes different methods for adaptive evolution of yeast strains to increase their fuel and chemical productions. The methods implemented consist of either sequential transfer of yeast from one vessel to another, or continuous culture of yeast in the same vessel. Furthermore, this publication notes that adaptive evolution generally occurs via a trade-off between the selected phenotypic trait and other physiological aspects of the organism; while there remains the risk of selecting a non-constitutive phenotypic trait, that is one induced by selective pressure but ceasing to be expressed when that pressure ceases to be applied. To circumvent these difficulties, the publication by Mans et al. emphasizes the need for dynamic evolutionary processes that expose organisms to different selective regimes. In particular, a strategy for alternating culture media when transferring from one vessel to another is described. However, this strategy involves exploring a single evolutionary pathway by alternating selective regimes sequentially.

International application WO 2018/152442 describes a method for adaptive evolution of liquid cultures of microorganisms in a programmable continuous culture system wherein a microbiological culture is subjected to a dynamic environment, said culture is exposed to a stress ramp function that is superimposed on a culture fitness function, and then the amount of stress applied to the microbiological culture is increased in response to the increased fitness of the microbiological culture.

However, the methods proposed in the prior art are time-consuming and tedious to implement and, above all, none of them allows rapid and efficient access to populations of microorganisms with a desired phenotype, especially a complex phenotype requiring the improvement of several phenotypic traits simultaneously.

Therefore, it appears necessary to develop a new method for adaptive evolution of living cells that makes it possible to quickly and effectively obtain living cells that have acquired a phenotype of interest.

DISCLOSURE OF THE INVENTION

The present invention thus has as its object a method for adaptive evolution of living cells excluding human embryonic stem cells, by continuously culturing said living cells in n culture vessels (RCi), i ranging from 1 to n, where n≥2, characterized in that said method comprises the following steps consisting of:

a) introducing at least one liquid culture medium and living cells into each of the n culture vessels,
b) in each of the n culture vessels, culturing said living cells according to a given selective regime, using predefined culture parameters, until a determined growth stage is reached in at least one of the n culture vessels, so as to obtain, in each of the n culture vessels, a suspension of living cells in said liquid culture medium,
c) combining at least a portion of the suspensions of living cells from at least two culture vessels (RCi) obtained in step b) to obtain a mixed suspension of living cells,
d) homogenizing the mixed suspension of living cells obtained in step c), to obtain a homogenized suspension of mixed living cells,
e) distributing at least part of the homogenized suspension of mixed living cells obtained in step d) into at least two culture vessels (RCi),
f) repeating steps b) to e),
g) collecting, after several culture cycles, living cells that have acquired a phenotype of interest in at least one of the culture vessels.

The inventors have surprisingly shown that the method according to the invention allows, through the parallel and multiplexed application of selective regimes, to select and collect living cells with phenotypes of interest. Advantageously, the method of the invention saves time compared to the simple or sequential use of these selective regimes. In particular, the repetition of steps b) to e), allowing the successive mixing of suspensions of living cells from at least two different culture vessels, and then their redistribution into new culture vessels, facilitates the progressive selection of the living cells that best react to the selective regime applied to them over the course of the culture cycles, and thus accelerates the attainment of a population of living cells that have acquired the phenotype of interest. This method thus increases the number of evolutionary paths that a suspension of living cells can take, increasing the probability and speed of the appearance of the phenotype of interest.

The present invention, among other things, addresses the needs for efficient evolution of living cells, which are particularly well suited to suspension culture conditions and optimized for manufacturing, degradation, or recycling of products.

The present invention is especially based on obtaining living cells well adapted to target conditions by frequently mixing fractions of living cell suspensions from different culture vessels which are grown in parallel under progressively increasing selective pressure according to different selective regimes and/or culture parameters.

For the purposes of the present invention, "continuous culture" means the culture of living cells carried out in at least one liquid culture medium, in which a fraction of said culture medium is renewed in order to keep the living cells growing for an extended period. Advantageously, the living cells are maintained for a large number of generations which is not defined in advance, advantageously greater than 2 generations, advantageously greater than 3 generations, advantageously greater than 4 generations, advantageously greater than 5 generations, advantageously greater than 6 generations, advantageously greater than 7 generations, advantageously greater than 8 generations, advantageously greater than 9 generations, advantageously greater than 10 generations, advantageously greater than 20 generations, advantageously greater than 30 generations, advantageously greater than 40 generations, advantageously greater than 50 generations, advantageously greater than 60 generations, advantageously greater than 70 generations, advantageously greater than 80 generations, advantageously greater than 90 generations, advantageously greater than 100 generations, advantageously greater than 150 generations, advantageously greater than 200 generations, advantageously greater than 250 generations, advantageously greater than 300 generations, advantageously greater than 130 generations, advantageously greater than 400 generations, advantageously greater than 450 generations, advantageously greater than 500 generations, advantageously greater than 550 generations, advantageously greater than 600 generations, advantageously greater than 650 generations, advantageously greater than 700 generations, advantageously greater than 750 generations, advantageously greater than 800 generations, advantageously greater than 850 generations, advantageously greater than 900 generations, advantageously greater than 950 generations, advantageously greater than 1000 generations, advantageously greater than 5000 generations, advantageously greater than 10,000 generations, advantageously greater than 15,000 generations, advantageously greater than 20,000 generations, advantageously greater than 25,000 generations, advantageously greater than 30,000 generations, advantageously greater than 35,000 generations, advantageously greater than 40,000 generations, advantageously greater than 45,000 generations, advantageously greater than 50,000 generations of living cells.

The renewal of the culture medium, or of a component of it (diluent), can be done permanently, regularly, or periodically. The medium can be renewed for one or more of the ingredients in its composition, or for the whole mixture of these ingredients. The medium is renewed so that at least 0.01% of the cells in culture are retained. Advantageously, the medium is renewed so that at least 0.1% of the cells in culture are in suspension, advantageously at least 1%, advantageously at least 2%, advantageously at least 3%, advantageously at least 4%, advantageously at least 5%, advantageously at least 6%, advantageously at least 7%, advantageously at least 8%, advantageously at least 9%, advantageously at least 10%, advantageously at least 11%, advantageously at least 12%, advantageously at least 13%, advantageously at least 14%, advantageously at least 15%, advantageously at least 16%, advantageously at least 17%, advantageously at least 18%, advantageously at least 19%, advantageously at least 20%, advantageously at least 21%, advantageously at least 22%, advantageously at least 23%, advantageously at least 24%, advantageously at least 25%, advantageously at least 26%, advantageously at least 27%, advantageously at least 28%, advantageously at least 29%, advantageously at least 30%, advantageously at least 31%, advantageously at least 32%, advantageously at least 33%, advantageously at least 34%, advantageously at least 35%, advantageously at least 36%, advantageously at least 37%, advantageously at least 38%, advantageously at least 39%, advantageously at least 40/a, advantageously at least 41%, advantageously at least 42%, advantageously at least 43%, advantageously at least 44%, advantageously at least 45%, advantageously at least 46%, advantageously at least 47%, advantageously at least 48%, advantageously at least 49%, advantageously at least 50%, advantageously at least 51%, advantageously at least 52%, advantageously at least 53%, advantageously at least 54%, advantageously at least 55%, advantageously at least 56%, advantageously at least 57%, advantageously at least 58%, advantageously at least 59%, advantageously at least 60%, advantageously at least 61%, advantageously at least 62%, advantageously at least 63%, advantageously at least 64%, advantageously at least 65%, advantageously at least 66%, advantageously at least 67%, advantageously at least 68%, advantageously at least 69%, advantageously at least 70%, advantageously at least 71%, advantageously at least 72%, advantageously at least 73%, advantageously at least 74%, advantageously at least 75%, advantageously at least 76%, advantageously at least 77%, advantageously at least 78%, advantageously at least 79%, advantageously at least 80%, advantageously at least 81%, advantageously at least 82%, advantageously at least 83%, advantageously at least 84%, advantageously at least 85%, advantageously at least 86%, advantageously at least 87%, advantageously at least 88%, advantageously at least 89%, advantageously at least 90%, advantageously at least 91%, advantageously at least 92%, advantageously at least 93%, advantageously at least 94%, advantageously at least 95%, advantageously at least 96%, advantageously at least 97%, advantageously at least 98%, advantageously at least 99% of the cells in culture are conserved.

For the purposes of the present invention, a "living cell that has acquired a phenotype of interest" or "cell variant" means a daughter cell that does not have the same physiological characteristics as its parent cell grown under the same conditions.

For the purposes of the present invention, a "method for adaptive evolution" is a process in which a population of living cells is exposed to a selective regime that promotes the acquisition of a phenotype of interest through the accumulation of advantageous physiological changes. Physiological changes can occur due to genetic modification (point mutation, loss or acquisition of genetic material) or epigenetic modification, and can result from stress or any other factor that can have a lasting impact on the behavior of living cells in culture.

The invention does not require that these physiological changes be predefined. On the contrary, the purpose of the invention is to promote the emergence of living cells that have acquired a phenotype of interest, without prior knowledge of the genetic and physiological modifications leading to said phenotype, and then to collect the living cells that have acquired a phenotype of interest, said phenotype conferring them a competitive advantage over the other cells, such as in particular surviving stress, growing under given conditions, possibly growing more rapidly under given conditions, making better use of the culture medium, or any other characteristic satisfying the industrial criteria.

For the purposes of the present invention, "selective pressures" means stress from a solubilized or gaseous toxic chemical compound, from an insufficiency of a solubilized or gaseous essential chemical compound, from an increase in temperature, from a decrease in temperature, from an increase in pH, from a decrease in pH, exposure to electromagnetic radiation of a particular wavelength, in particular exposure to ultraviolet radiation, exposure to infrared radiation, exposure to electromagnetic radiation of a wavelength lethal to the cell, exposure to a mutagenic agent, or a combination of these stresses, all of which result in either a decrease in productivity, for example by increasing the doubling time of the living cells, or a decrease in yield, for example by decreasing the amount of living cells produced, or extinction of the living cells.

For the purposes of the present invention, "cell" or "cells" or "living cell" or "living cells" or "population of living cells" means one or more small biological entities comprising a cytoplasm bounded by a membrane and having the ability to reproduce autonomously. Advantageously, the living cells can be eukaryotic or prokaryotic, human, animal or vegetable, with the exception of human embryonic stem cells. Microorganisms are considered cells. Advantageously, the living cells are selected from mammalian cells, insect cells, bacteria, yeast, microalgae, plant cells, fungi, and microbes. For the purposes of the present invention, "microalgae" means single-celled algae. Advantageously, by living cells, we also mean eukaryotic or prokaryotic cells, human, animal or vegetable, with the exception of human embryonic stem cells, possibly infected by a virus, a phage or a parasite and/or having integrated one or more plasmids of interest.

For the purposes of the present invention, "culture vessel" or "culture chamber" or "culture reservoir" means a container wherein living cells are cultured in a culture medium according to a given selective regime, establishing the modalities under which the culture conditions are set according to operating rules based in particular on predefined culture parameters, until a given growth stage is reached. In a particular embodiment, the culture vessel is recyclable. In a particular embodiment, the culture vessel is disposable.

For the purposes of the present invention, "suspension" means a liquid culture medium containing living cells.

According to the invention, step c) consisting of combining at least part of the suspensions of living cells from at least two culture vessels (Ri) obtained in step b) can be carried out either by using one of said at least two culture vessels as a mixing vessel, or in a mixing vessel independent of the at least two culture vessels and making it possible to accommodate all or some of the contents of said at least two culture vessels.

For the purposes of the present invention, "mixing vessel" or "mixing reservoir" means a container wherein the contents of at least two culture vessels are mixed. Thus, a mixing vessel contains at least the suspension from a first culture vessel and the suspension from a second culture vessel. Advantageously, the method according to the invention may comprise as many mixing vessels as culture vessels. Advantageously, the number of mixing vessels may vary from 1 to n. In a particular embodiment, the number of mixing vessels is at least 2. In a particularly advantageous embodiment, the number of mixing vessels is equal to 3. In another particularly advantageous embodiment, the number of mixing vessels is equal to 4. In another particularly advantageous embodiment, the number of mixing vessels is equal to 5. In another particularly advantageous embodiment, the number of mixing vessels is equal to 6. In another particularly advantageous embodiment, the number of mixing vessels is equal to 7. In another particularly advantageous embodiment, the number of mixing vessels is equal to 8. In another particularly advantageous embodiment, the number of mixing vessels is equal to 9. In another particularly advantageous embodiment, the number of mixing vessels is equal to 10.

In a particular embodiment, the mixing vessel is recyclable. In a particular embodiment, the mixing vessel is disposable.

In step a), at least one volume of liquid culture medium and a specific quantity of living cells are introduced into each of the n culture vessels. Advantageously, specific quantity of living cells means at least one living cell, at least 10 living cells, advantageously at least 20 living cells, advantageously at least 30 living cells, advantageously at least 40 living cells, advantageously at least 50 living cells, advantageously at least 60 living cells, advantageously at least 70 living cells, advantageously at least 80 living cells, advantageously at least 90 living cells, advantageously at least 100 living cells, advantageously at least 200 living cells, advantageously at least 300 living cells, advantageously at least 400 living cells, advantageously at least 500 living cells, advantageously at least 600 living cells, advantageously at least 700 living cells, advantageously at least 800 living cells, advantageously at least 900 living cells, advantageously at least 1000 living cells, advantageously at least $10^4$living cells, advantageously at least $10^5$ living cells, advantageously at least $10^6$ living cells, advantageously at least $10^7$ living cells, advantageously at least $10^8$ living cells, advantageously at least $10^9$ living cells, advantageously at least $10^{10}$ living cells, advantageously at least $10^{11}$ living cells, advantageously at least $10^{12}$ living cells.

In a particular embodiment of the invention, the at least one culture medium comprises nutrients essential for the growth of living cells. The person skilled in the art will know how to adapt the at least one culture medium, and in particular its composition, based on the type of living cells used. Advantageously, the at least one culture medium is a fresh, sterile culture medium.

In a particular embodiment of the invention, the at least one culture medium and the living cells are introduced into each of the n culture vessels via supply means, for example pumps and valves connected by lines, making it possible to connect the culture medium reservoirs to each of the n culture vessels.

In step b), said determined growth stage can be reached at the end of a predefined period of time, linked to the cell density or to a physical/chemical indicator measurable in the culture medium such as pH, fluorescence, radioactivity, the concentration of a molecule produced, the concentration of a molecule consumed, such as nutrients, the presence of a toxic agent, the dilution rate, the number of injections of stress culture medium, the time elapsed between two injections of culture medium, etc.

This "determined growth stage" can be based on the target phenotype or on typical growth curves, established in advance, either experimentally or from literature data.

In a particular embodiment, cell density can be measured by optical measurement.

In a particularly advantageous embodiment, a particular value of a measurable physical/chemical indicator is set, for example, a cell density threshold, a particular dilution rate, a number of injections of stress culture medium, the time elapsed between two injections of culture medium, a particular pH, a particular temperature, a particular gas composition agitating the suspension, a particular fluorescence, a particular radioactivity, an electromagnetic or radioactive radiation at a particular intensity and frequency, a particular produced molecule concentration, a particular nutrient concentration, a particular growth factor concentration, a particular toxic agent concentration.

The method provides that after seeding the culture medium, the living cells grow to the set value. When this critical value is reached for at least one of the culture vessels, the culture, that is all or part of the suspension consisting of the culture medium and the living cells, is transferred to at least one mixing vessel.

In another particular embodiment, said determined growth stage may be related to a period of predefined duration. Advantageously, the period of predefined duration is fixed can be 1 minute, advantageously 2 minutes, advantageously 3 minutes, advantageously 4 minutes, advantageously 5 minutes, advantageously 6 minutes, advantageously 7 minutes, advantageously 8 minutes, advantageously 9 minutes, advantageously 10 minutes, advantageously 15 minutes, advantageously 20 minutes, advantageously 25 minutes, advantageously 30 minutes, advantageously 35 minutes, advantageously 40 minutes, advantageously 45 minutes, advantageously 50 minutes, advantageously 55 minutes, advantageously 60 minutes, advantageously 65 minutes, advantageously 70 minutes, advantageously 75 minutes, advantageously 80 minutes, advantageously 85 minutes, advantageously 90 minutes, advantageously 95 minutes, advantageously 100 minutes, advantageously 105 minutes, advantageously 110 minutes, advantageously 115 minutes, advantageously after 120 minutes, advantageously 3 hours, advantageously 4 hours, advantageously 5 hours, advantageously 6 hours, advantageously 7 hours of culture, advantageously 8 hours, advantageously 9 hours of culture, advantageously 10 hours, advantageously 11 hours of culture, advantageously 12 hours, advantageously 13 hours of culture, advantageously 14 hours, advantageously 15 hours of culture, advantageously 16 hours, advantageously 17 hours of culture, advantageously 18 hours, advantageously 19 hours of culture, advantageously 20 hours, advantageously 21 hours of culture, advantageously 22 hours, advantageously 23 hours of culture, advantageously 24 hours, the list not being limiting.

Advantageously, said determined growth stage can be reached after 1 minute of culture, advantageously after 2 minutes, advantageously after 3 minutes, advantageously after 4 minutes, advantageously after 5 minutes, advantageously after 6 minutes, advantageously after 7 minutes, advantageously after 8 minutes, advantageously after 9 minutes, advantageously after 10 minutes, advantageously after 15 minutes, advantageously after 20 minutes, advantageously after 25 minutes, advantageously after 30 minutes, advantageously after 35 minutes, advantageously after 40 minutes, advantageously after 45 minutes, advantageously after 50 minutes, advantageously after 55 minutes, advantageously after 60 minutes, advantageously after 65 minutes, advantageously after 70 minutes, advantageously after 75 minutes, advantageously after 80 minutes, advantageously after 85 minutes, advantageously after 90 minutes, advantageously after 95 minutes, advantageously after 100 minutes, advantageously after 105 minutes, advantageously after 110 minutes, advantageously after 115 minutes, advantageously after 120 minutes, advantageously after 3 hours, advantageously after 4 hours, advantageously after 5 hours, advantageously after 6 hours, advantageously after 7 hours, advantageously after 8 hours, advantageously after 9 hours, advantageously after 10 hours, advantageously after 11 hours, advantageously after 12 hours, advantageously after 13 hours, advantageously after 14 hours, advantageously after 15 hours, advantageously after 16 hours, advantageously after 17 hours, advantageously after 18 hours, advantageously after 19 hours, advantageously after 20 hours, advantageously after 21 hours, advantageously after 22 hours, advantageously after 23 hours, advantageously after 24 hours of culture, the list not being limiting.

In this case, the method provides that after seeding the culture medium, the living cells grow for a set predefined period of time. When this culture time is reached, the culture, that is all or part of the suspension consisting of the culture medium and the living cells, is transferred to at least one mixing vessel.

In a particular embodiment of the method according to the invention, in step b), the living cells are cultured in a selective regime, said selective regime being selected from: chemostat, turbidostat, medium swap, and iterated batch.

For the purposes of the present invention, “chemostat conditions” or “chemostat” means a type of cell culture wherein a single culture medium containing at least one essential nutrient in limited content, preferentially sterile, is used to dilute the cells and wherein the flow rate of the culture medium is constant. Advantageously, culture medium is fed at a predefined rate continuously, that is without interruption, into said culture vessel keeping the volume of said vessel constant to dilute the cells. Alternatively, at regular intervals, a predefined volume of culture medium is sent to said culture vessel to dilute the cells.

For the purposes of the present invention, “regular intervals” means every 30 seconds, advantageously every 35 seconds, advantageously every 40 seconds, advantageously every 45 seconds, advantageously every 50 seconds, advantageously every 55 seconds, advantageously every 1 minute, advantageously every 2 minutes, advantageously every 3 minutes, advantageously every 4 minutes, advantageously every 5 minutes, advantageously every 10 minutes, advantageously every 15 minutes, advantageously every 20 minutes, advantageously every 25 minutes, advantageously every 30 minutes.

For the purposes of the present invention, “turbidostat conditions” or “turbidostat” means a type of cell culture wherein a single culture medium containing all essential nutrients in excess, preferentially sterile, is used to dilute the cells and wherein a constant cell density is maintained within the at least one culture vessel. Advantageously, culture medium is fed at a variable rate continuously, that is without interruption, into said culture vessel keeping the volume of said vessel constant to dilute the cells so as to maintain a turbidity at said threshold value. Alternatively, at regular intervals, the cell density of the culture is measured in the at least one culture vessel and compared to a threshold value. If the measured cell density is below the threshold value, then the culture is continued until the end of the next interval. If the measured cell density is above the threshold value, then a predefined volume of culture medium is sent to said culture vessel to dilute the cells.

For the purposes of the present invention, “medium swap” means a type of cell culture regime wherein two different, preferentially sterile, culture media, one called a permissive culture medium and the other called stressing culture medium, are used to dilute the cells by adding medium to said culture vessel while keeping the volume of said vessel constant and in a semi-continuous manner. If so, at regular intervals, the cell density of the culture is measured in the at least one culture vessel and compared to a threshold value. If the measured cell density is below the threshold value, then a predefined volume of permissive culture medium is sent to the culture vessel. If the measured cell density is above the threshold value, then the predefined volume of stressing culture medium is sent to the culture vessel. The medium swap can be performed as described in Döring et al, (ACS Synthetics Biology, 2018, vol 7(9), pages 2029-2036).

In a particular embodiment of the invention, the at least one culture medium may be a so-called “permissive” culture medium or a so-called “stressing” culture medium. A “permissive culture medium” is a culture medium perfectly adapted to cell growth, comprising nutrients and growth factors essential to cell growth and free of toxic agents that can cause cell death, such as cell growth inhibitors, or present in an amount that is not lethal to said cells. A “stressing culture medium” is a culture medium comprising nutrients essential for cell growth and wherein either a toxic agent is present in an amount capable of causing cell death, such as cell growth inhibitors, or a growth factor essential for cell growth is absent, or the amount of toxic agent is present in a non-negligible proportion and a growth factor essential for cell growth is missing, or wherein the substrate is not a preferred substrate of said cells.

For the purposes of the present invention, “iterated batch” means a type of cell culture regime wherein a culture medium, preferentially a sterile one, is used to dilute the cells. In this case, the cells grow in the at least one culture vessel without any dilution of the culture medium until a predetermined cell density value is reached. When the cell density value is reached, the suspension is maintained for a predetermined culture time. When the time after reaching the cell density threshold is reached in said culture vessel, a volume of sterile culture medium is sent to said culture vessel at constant volume. In an alternative embodiment, when the time after reaching the cell density threshold is reached in said culture vessel, a fraction of the suspension from said culture vessel is sent to at least one different culture vessel, already containing growth medium, preferentially sterile.

In a particular embodiment, in step b), the living cells are cultured in the chemostat selective regime.

In a particular embodiment, in step b), the living cells are cultured in the turbidostat selective regime.

In a particular embodiment, in step b), the living cells are cultured in the medium swap selective regime.

In a particular embodiment, in step b), the living cells are cultured in the iterated batch selective regime.

In a particularly advantageous embodiment, the selective regime used in step b) of the method according to the invention may be identical for all n culture vessels.

In a particularly advantageous embodiment, the selective regime used in step b) of the method according to the invention may be different from one culture vessel to another. In a particular embodiment of the invention, different selective regimes can be used in the culture step b) between the n culture vessels. Advantageously, it is possible to use two different selective regimes, advantageously three different selective regimes, advantageously four different selective regimes, advantageously five different selective regimes between the n culture vessels.

In a particular embodiment of the method according to the invention, in step b), the living cells are cultured in a selective regime as defined above, using predefined culture parameters, until they reach a determined growth stage in at least one of the n culture vessels, so as to obtain a suspension. In a particular embodiment of the method according to the invention, the predefined culture parameters of step b) are selected from: dilution rate, temperature, pH, cell density, culture medium composition, gas stream composition, exposure to electromagnetic radiation of a particular wavelength, exposure to a mutagenic agent, or a combination thereof.

According to the invention, "different selective regime" means either a selective regime of the same nature but of different intensity, or a selective regime of a different nature regardless of its intensity. Thus, and by way of example, when the selective regime is the pH, it can take on different values from one culture vessel to another. According to another example, the selective regime is also different when in a given culture vessel the living cells are subjected to a particular selective regime such as the influence of pH and in the other culture vessel the living cells are subjected to another particular selective regime such as the influence of temperature.

For the purposes of the present invention, "exposure to electromagnetic radiation of a particular wavelength" means exposure to electromagnetic radiation of visible wavelength, that is wavelength between 400 nm and 800 nm, exposure to ultraviolet radiation, that is wavelength less than 400 nm, exposure to infrared radiation, that is wavelength greater than 800 nm, or even exposure to electromagnetic radiation of a wavelength that is lethal to the cell.

For the purposes of the present invention, "mutagenic agent" means a chemical agent causing a mutation of the insertion, deletion or substitution type in the genome of the cell. Advantageously, the mutagenic agent may be selected from alkylating agents, such as N-nitroso-N-ethylurea (also referred to as N-ethyl-N-nitrosourea (ENU)) or ethyl methanesulfonate (also referred to as ethyl methanesulfonate (EMS)), intercalating agents, such as proflavin and acridine orange, and reactive oxygen species, including free radicals, oxygen ions, and peroxides.

In a particularly advantageous embodiment, the selective regimes used in step b) of the method according to the invention may be identical for all of the n culture vessels.

In a particularly advantageous embodiment, the selective regimes used in step b) of the method according to the invention may be different from one culture vessel to another.

In a particularly advantageous embodiment, the culture parameters used in step b) of the method according to the invention may be identical for all of the n culture vessels.

In a particularly advantageous embodiment, the culture parameters used in step b) of the method according to the invention may be different from one culture vessel to another.

Advantageously, for the remainder of the presentation, we will denote, for all of the culture vessels (RCi):

- T0i, the initial temperature used in step b) in the culture vessel RCi,
- pH(i,k), the initial pH used in step b) in the culture vessel RCi,
- DO(i,k), the initial cell density used in step b) in the culture vessel RCi,
- MC(i,k), the composition of the at least one initial culture medium used in step b) in the culture vessel RCi,
- G(i,k), the composition of the initial gas stream used in step b) in the culture vessel RCi,
- λ(i,k), the exposure to electromagnetic radiation of a particular initial wavelength used in step b) in the culture vessel RCi,
- Td(i,k), the initial dilution rate used in step b) in the culture vessel Rci, and
- AM(i,k), the initial exposure to a mutagenic agent used in step b) in the culture vessel RCi.

Advantageously, during step b), the cells are cultured at temperature T0i, at a pH equal to pH(i,k), a cell density DOk(i,k), in at least one culture medium of composition MC(i,k), at a dilution rate Td(i,k) and in the presence of gas of composition G(i,k) for all of the n culture vessels.

According to a particular embodiment, the culture method may provide that a gas stream is injected under pressure into the suspension by means of a gas supply device, for example in the form of aeration rods introduced into the culture vessel. This injection of gas stream allows the aeration of the suspension, the homogenization of the said suspension (agitation by bubbling) and contributes to maintain a certain gas pressure inside the culture vessel. According to the method, the culture vessel is advantageously traversed by a sterile gas stream. This gas stream can be constituted by a gas, chosen among air, nitrogen ($N_2$), carbon monoxide (CO), carbon dioxide ($CO_2$), methane ($CH_4$), hydrogen sulfide ($H_2S$), oxygen ($O_2$), nitrous oxide ($N_2O$), dihydrogen ($H_2$) or a mixture of these gases, according to the chosen culture parameters.

According to a particular embodiment, the culture method may provide a means for mechanically agitating the suspension in the culture vessel.

In step c), as soon as the determined growth stage is reached in step b), all or part of the suspension contained in at least one culture vessel is combined with all or some of the suspension contained in at least one other culture vessel. As previously mentioned, the combining of the suspensions can be performed either in one of the at least two culture vessels, which thereby serves as a mixing vessel, the internal volume of said culture vessel then being sufficient to accommodate all or part of the suspension coming from the at least one other culture vessel, or in at least one independent mixing vessel having an internal volume to accommodate all or part of each of the suspensions of said at least two culture vessels.

In a particular embodiment of the invention, all or a portion of the suspension contained in at least three culture vessels, advantageously all or a portion of the suspension contained in at least four culture vessels, advantageously all or part of the suspension contained in at least n culture vessels is transferred to the at least one mixing vessel.

In a particular embodiment of the invention, in step c) only a part of each of the suspensions contained in at least two culture vessels is combined.

Advantageously, for the purposes of the present invention, "a part of the suspension" is understood to mean at least 1% of the suspension contained in the culture vessel, advantageously at least 2%, advantageously at least 3%, advantageously at least 4%, advantageously at least 5%, advantageously at least 6%, advantageously at least 7%, advantageously at least 8%, advantageously at least 9%, advantageously at least 10%, advantageously at least 11%, advantageously at least 12%, advantageously at least 13%, advantageously at least 14%, advantageously at least 15%, advantageously at least 16%, advantageously at least 17%, advantageously at least 18%, advantageously at least 19%, advantageously at least 20%, advantageously at least 21%, advantageously at least 22, advantageously at least 23%, advantageously at least 24%, advantageously at least 25%, advantageously at least 26%, advantageously at least 27%, advantageously at least 28%, advantageously at least 29%, advantageously at least 30%, advantageously at least 31%, advantageously at least 32%, advantageously at least 33%, advantageously at least 34%, advantageously at least 35%, advantageously at least 36%, advantageously at least 37%, advantageously at least 38%, advantageously at least 39%, advantageously at least 40%, advantageously at least 41%, advantageously at least 42%, advantageously at least 43%, advantageously at least 44%, advantageously at least 45%, advantageously at least 46%, advantageously at least 47%, advantageously at least 48%, advantageously at least 49%, advantageously at least 50%, advantageously at least 51%, advantageously at least 52%, advantageously at least 53%, advantageously at least 54%, advantageously at least 55%, advantageously at least 56%, advantageously at least 57%, advantageously at least 58%, advantageously at least 59%, advantageously at least 60%, advantageously at least 61%, advantageously at least 62%, advantageously at least 63%, advantageously at least 64%, advantageously at least 65%, advantageously at least 66%, advantageously at least 67%, advantageously at least 68%, advantageously at least 69%, advantageously at least 70%, advantageously at least 71%, advantageously at least 72%, advantageously at least 73%, advantageously at least 74%, advantageously at least 75%, advantageously at least 76%, advantageously at least 77%, advantageously at least 78%, advantageously at least 79%, advantageously at least 80%, advantageously at least 81%, advantageously at least 82%, advantageously at least 83%, advantageously at least 84%, advantageously at least 85%, advantageously at least 86%, advantageously at least 87%, advantageously at least 88%, advantageously at least 89%, advantageously at least 9%, advantageously at least 91%, advantageously at least 92%, advantageously at least 93%, advantageously at least 94%, advantageously at least 95%, advantageously at least 96%, advantageously at least 97%, advantageously at least 98%, advantageously at least 99% of the suspension contained in the culture vessel.

In another embodiment of the invention, and when step c) is performed using a mixing vessel, then a transfer of at least a portion of the suspension obtained in step b) from at least two culture vessels to at least one mixing vessel is carried out. According to this embodiment, the suspension fractions transferred from each of the culture vessels to the at least one mixing vessel may be the same or different.

In an advantageous embodiment of the invention, the at least one mixing vessel is an arranged culture vessel, that is the interior volume of which is sufficient to accommodate the contents of at least two culture vessels. Advantageously, the at least one mixing vessel is a culture vessel arranged to receive the contents of at least three culture vessels, advantageously at least four culture vessels, advantageously at least n culture vessels. Advantageously, “contents of at least one culture vessel” means the suspension obtained in step b) and present in at least one culture vessel. Advantageously, “contents of at least two culture vessels” means the suspension obtained in step b) contained and present in at least two culture vessels.

In an advantageous embodiment of the invention, the at least one mixing vessel is a single vessel, independent of the set of culture vessels, and arranged to receive the contents of the set of culture vessels.

In a particular embodiment of the invention, and when step c) comprises an operation of transferring the suspensions to at least one mixing vessel, then the transfer of all or part of each of the suspensions from said at least two culture vessels to the at least one mixing vessel may be performed by transfer means, said transfer means being able to comprise in particular one or more pumps, one or more valves, one or more injections of a gaseous flow, one or more pipetting robots or a combination of these means.

Advantageously, the pump(s) can be for example mechanically operated or can be electrically or electronically controlled, advantageously automatically using control means. Advantageously, the pump(s) can be peristaltic pumps driven by a control unit, advantageously driven by an automaton or by a computer.

Advantageously, the valve(s) can be for example mechanically operated or can be electrically or electronically controlled, advantageously automatically using control means. Advantageously, the valve(s) can be solenoid valves driven by a control unit, advantageously driven by an automaton or by a computer.

Advantageously, the injection of a gas stream can be implemented for example from a gas supply device present on the culture vessels or from an external gas source.

In a particular embodiment of the invention, and when step c) comprises a transfer operation, then said transfer is performed using one or more pumps and one or more valves.

In another particular embodiment of the invention, and when step c) comprises a transfer operation, then said transfer is performed using one or more valves and one or more injections of a gas stream, for example generated by pressure differences.

In a particular embodiment of the invention, and when step c) comprises a transfer operation, then said transfer is performed using one or more pipetting robots.

Step d) of the method consists of homogenizing the mixture resulting from the combination of all or part of the suspensions of living cells from at least 2 culture vessels according to step c). According to the present invention, the homogenization step results in a suspension of living cells wherein the distribution in the volume of the mixing vessel of the cells from each of the at least two culture vessels is random.

In a particular embodiment of the invention, the homogenization step d) is carried out in whole or in part by an agitation means selected in particular from a mechanical agitator and an injection of a gas stream.

In a particular embodiment of the invention, the homogenization step d) is carried out, in whole or in part, by means of an injection of a gas stream, said gas stream being injected under pressure into the vessel containing the mixed cell suspension of step c) by means of a gas supply device. This injection of gas stream allows the homogenization of the mixture of suspensions by agitation by bubbling (for example by using the principle of air-lift). Advantageously, this gas stream can be constituted by a gas, chosen among air, nitrogen ($N_2$), carbon monoxide (CO), carbon dioxide ($CO_2$), methane ($CH_4$), hydrogen sulfide ($H_2S$), oxygen ($O_2$), nitrous oxide ($N_2O$), dihydrogen ($H_2$) or a mixture of these gases, according to the chosen culture parameters.

Preferably, step e) of the method consists of transferring at least a portion of the homogenized suspension of mixed living cells obtained in step d) to at least two culture vessels (RCi).

In a particularly advantageous embodiment of the invention, the at least part of the suspension transferred in step e) corresponds to a fraction between 1 and 100% of the homogenized suspension of mixed living cells.

Advantageously, the fraction of the volume of the homogenized suspension of mixed living cells transferred to step e) represents at least 1% of the total volume of said homogenized suspension, advantageously at least 2%, advantageously at least 3%, advantageously at least 4%, advantageously at least 5%, advantageously at least 6%, advantageously at least 7%, advantageously at least 8%, advantageously at least 9%, advantageously at least 10%, advantageously at least 11%, advantageously at least 12%, advantageously at least 13%, advantageously at least 14%, advantageously at least 15%, advantageously at least 16%, advantageously at least 17%, advantageously at least 18%, advantageously at least 19%, advantageously at least 20%, advantageously at least 21%, advantageously at least 22%, advantageously at least 23%, advantageously at least 24%, advantageously at least 25%, advantageously at least 26%, advantageously at least 27%, advantageously at least 28%, advantageously at least 29%, advantageously at least 30%, advantageously at least 31%, advantageously at least 32%, advantageously at least 33%, advantageously at least 34%, advantageously at least 35%, advantageously at least 36%, advantageously at least 37%, advantageously at least 38%, advantageously at least 39%, advantageously at least 40%, advantageously at least 41%, advantageously at least 42%, advantageously at least 43%, advantageously at least 44%, advantageously at least 45%, advantageously at least 46%, advantageously at least 47%, advantageously at least 48%, advantageously at least 49%, advantageously at least 50%, advantageously at least 51%, advantageously at least 52%, advantageously at least 53%, advantageously at least 54%, advantageously at least 55%, advantageously at least 56%, advantageously at least 57%, advantageously at least 58%, advantageously at least 59%, advantageously at least 60%, advantageously at least 61%, advantageously at least 62%, advantageously at least 63%, advantageously at least 64%, advantageously at least 65%, advantageously at least 66%, advantageously at least 67%, advantageously at least 68%, advantageously at least 69%, advantageously at least 70%, advantageously at least 71%, advantageously at least 72%, advantageously at least 73%, advantageously at least 74%, advantageously at least 75%, advantageously at least 76%, advantageously at least 77%, advantageously at least 78%, advantageously at least 79%, advantageously at least 80%, advantageously at least 81%, advantageously at least 82%, advantageously at least 83%, advantageously at least 84%, advantageously at least 85%, advantageously at least 86%, advantageously at least 87%, advantageously at least 88%, advantageously at least 89%, advantageously at least 90%, advantageously at least 91%, advantageously at least 92%, advantageously at least 93%, advantageously at least 94%, advantageously at least 95%, advantageously at least 96%, advantageously at least 97%, advantageously at least 98%, advantageously at least 99%, advantageously 100% of the total volume of said homogenized suspension.

In another embodiment of step e) according to the method of the invention, when transferring at least a portion of the suspension obtained in step d) to n culture vessels, the fraction of the volume of homogenized suspension of mixed living cells transferred to each of the n culture vessels may be the same or different.

In a particular embodiment of the invention, the method according to the invention comprises n culture vessels (RCi), i ranging from 1 to n, n being at least equal to 2, and at least n−1 mixing vessels (RMj), j ranging from 1 to n−1, the at least n−1 mixing vessels being respectively a culture vessel (RCi) arranged to receive the contents of at least two culture vessels, said method being further characterized in that steps c) to e) are carried out as follows:

i) transferring all or part of the suspension obtained in step b) from a culture vessel (RCi), known as the starting culture vessel, to a mixing vessel (RMj), known as the destination vessel, so as to perform a destination transfer, ii) homogenizing the suspension from the starting culture vessel (RCi) with that of the destination vessel (RMj) in the destination vessel (RMj), to obtain a homogenized suspension of mixed living cells, iii) transferring at least part of the suspension obtained in step ii) from the destination vessel (RMj) to the starting culture vessel (RCi), so as to perform a return transfer, iv) repeating the preceding steps i) to iii) while varying RCi and RMj so that all suspensions have been combined 2-by-2 at least once.

In a particularly advantageous embodiment, n is equal to 3. In another particularly advantageous embodiment, n is equal to 4. In another particularly advantageous embodiment, n is equal to 5. In another particularly advantageous embodiment, n is equal to 6. In another particularly advantageous embodiment, n is equal to 7. In another particularly advantageous embodiment, n is equal to 8. In another particularly advantageous embodiment, n is equal to 9. In another particularly advantageous embodiment, n is equal to 10.

Advantageously, the method according to the invention comprises three culture vessels, a first culture vessel RC1, a second culture vessel RC2, a third culture vessel RC3, the three culture vessels serving successively as mixing vessels RM1, RM2 and RM3, each culture vessel being arranged to receive the contents of the other two culture vessels, the method being characterized in that steps c) to e) are carried out as follows:

i) transferring the suspension of living cells from the first culture vessel RC1 to the second culture vessel RC2, which then also serves as the first mixing vessel RM1, so as to perform a destination transfer, ii) homogenizing the suspensions from the first culture vessel RC1 and the second culture vessel RC2 in the second culture vessel RC2, which then serves as the first mixing vessel RM1 (RC2=RM1), to obtain a homogenized suspension of mixed living cells, iii) transferring at least part of the suspension from the first mixing vessel RM1, to the first culture vessel RC1, so as to perform a return transfer, iv) transferring the suspension from the third culture vessel RC3 to the first culture vessel RC1, which then also serves as the second mixing vessel RM2, so as to perform a destination transfer, v) homogenizing the suspensions from the third culture vessel RC3 and the first culture vessel RC1 in the first culture vessel RC1, which then serves as the second mixing vessel RM2 (RC1=RM2), to obtain a homogenized suspension of mixed living cells, vi) transferring at least part of the suspension from the second mixing vessel RM2, to the third culture vessel RC3, so as to perform a return transfer, vii) transferring the suspension from the second culture vessel RC2 to the third culture vessel RC3, which then also serves as the third mixing vessel RM3, so as to perform a destination transfer, viii) homogenizing the suspensions from the second culture vessel RC2 and the third culture vessel RC3 in the third culture vessel RC3, which then serves as the third mixing vessel RM3 (RC3=RM3), to obtain a homogenized suspension of mixed living cells, ix) transferring at least part of the suspension from the third mixing vessel RM3, to the second culture vessel RC2, so as to perform a return transfer.

In another particular embodiment of the invention, the method according to the invention comprises n culture vessels (RCi), i ranging from 1 to n, n being at least equal to 2, and at least n−1 mixing vessels (RMj), j ranging from 1 to n−1, the at least n−1 mixing vessels being respectively a culture vessel (RCi) arranged to receive the contents of at least two culture vessels, characterized in that steps c) to e) are carried out as follows:

i) transferring all or part of the suspension of living cells obtained in step b) from a culture vessel (RCi), known as the starting culture vessel, to a mixing vessel (RMj), known as the destination vessel, so as to perform a destination transfer, ii) homogenizing the suspension from the starting culture vessel (RCi) with that of the destination vessel (RMj) in the destination vessel (RMj), to obtain a homogenized suspension of mixed living cells, iii) transferring at least part of the suspension obtained in step ii) from the destination vessel (RMj) to the starting culture vessel (RCi), so as to perform a return transfer, iv) repeating the preceding steps i) to iii) n−(i+1) times while incrementing j by one unit at each repetition so as to transfer all or part of the suspension from the starting culture vessel (RCi) to a destination vessel RMj+1 so as to perform n−(i+1) further destination transfers and n−(i+1) further return transfers, v) repeating steps i) to iv) n−(i+1) times while incrementing i by one at each repetition so that the starting culture vessel becomes RCi+1 after each end of step v).

In a particularly advantageous embodiment, n is equal to 3. In another particularly advantageous embodiment, n is equal to 4. In another particularly advantageous embodiment, n is equal to 5. In another particularly advantageous embodiment, n is equal to 6. In another particularly advantageous embodiment, n is equal to 7. In another particularly advantageous embodiment, n is equal to 8. In another particularly advantageous embodiment, n is equal to 9. In another particularly advantageous embodiment, n is equal to 10.

Advantageously, the method according to the invention comprises three culture vessels, namely a first culture vessel RC1, a second culture vessel RC2, a third culture vessel RC3, the second and third culture vessels (RC2 and RC3) serving successively as mixing vessels RM1 and RM2, each culture vessel RC2 and RC3 being arranged to receive the contents of two culture vessels, the method being characterized in that steps c) to e) are carried out as follows:

i) transferring the suspension of living cells obtained in step b) from the first culture vessel RC1 to the second culture vessel RC2, which then also serves as the first mixing vessel RM1, so as to perform a destination transfer, ii) homogenizing the suspensions from the first culture vessel RC1 and the second culture vessel RC2 in said culture vessel RC2, which then serves as the first mixing vessel RM1, to obtain a homogenized suspension of mixed living cells, iii) transferring at least part of the suspension from the first mixing vessel RM1, to the first culture vessel RC1, so as to perform a return transfer, iv) transferring the suspension from the first culture vessel RC1 to the third culture vessel RC3, which then also serves as the second mixing vessel RM2, so as to perform a destination transfer, v) homogenizing the suspensions from the first culture vessel RC1 and the third culture vessel RC3 in said third culture vessel, which then serves as the second mixing vessel RM2, to obtain a homogenized suspension of mixed living cells, vi) transferring at least part of the suspension from the second mixing vessel RM2, to the first culture vessel RC1, so as to perform a return transfer, vii) transferring the suspension from the second culture vessel RC2 to the third culture vessel RC3, which then also serves as the second mixing vessel RM2, so as to perform a destination transfer, viii) homogenizing the suspensions from the second culture vessel RC2 and the third culture vessel RC3 in said third culture vessel RC3 which then serves as the second mixing vessel RM2, ix) transferring at least part of the suspension from the second mixing vessel RM2, to the second culture vessel RC2, so as to perform a return transfer.

In another particular embodiment of the invention, the method according to the invention uses n culture vessels (RCi), i ranging from 1 to n, n being at least equal to 2, and at least one mixing vessel, the at least one mixing vessel being a single vessel independent of the set of culture vessels, and being arranged to receive the contents of the n culture vessels, characterized in that steps c) to e) are carried out as follows:

c) transferring all or part of the suspension of living cells obtained in step b) from at least two culture vessels to the at least one mixing vessel, to obtain a mixed suspension of living cells, d) homogenizing the mixed suspension of living cells obtained in step c) in the at least one mixing vessel (RM), to obtain a homogenized mixed suspension of living cells, e) transferring at least a portion of the suspension obtained in step d) from the at least one mixing vessel to each of the at least two culture vessels.

In a particularly advantageous embodiment, n is equal to 3. In another particularly advantageous embodiment, n is equal to 4. In another particularly advantageous embodiment, n is equal to 5. In another particularly advantageous embodiment, n is equal to 6. In another particularly advantageous embodiment, n is equal to 7. In another particularly advantageous embodiment, n is equal to 8. In another particularly advantageous embodiment, n is equal to 9. In another particularly advantageous embodiment, n is equal to 10.

The use of a single mixing vessel, independent of the culture vessels and arranged to receive the contents of the n culture vessels, makes it possible to speed up the mixing step d) while being simpler to implement.

In a particularly advantageous embodiment of the invention, the at least part of the suspension transferred in step e) to each of the at least two culture vessels corresponds to a fraction of the volume of the homogenized suspension of mixed living cells, said volume fraction being between 1 and 100% of the total volume of said suspension.

Advantageously, the fraction of the volume of the homogenized suspension of mixed living cells transferred in step e) represents at least 1% of the total volume of said suspension, advantageously at least 2%, advantageously at least 3%, advantageously at least 4%, advantageously at least 5%, advantageously at least 6%, advantageously at least 7%, advantageously at least 8%, advantageously at least 9%, advantageously at least 10%, advantageously at least 11%, advantageously at least 12%, advantageously at least 13%, advantageously at least 14%, advantageously at least 15%, advantageously at least 16%, advantageously at least 17%, advantageously at least 18%, advantageously at least 19%, advantageously at least 20%, advantageously at least 21%, advantageously at least 22%, advantageously at least 23%, advantageously at least 24%, advantageously at least 25%, advantageously at least 26%, advantageously at least 27%, advantageously at least 28%, advantageously at least 29%, advantageously at least 30%, advantageously at least 31%, advantageously at least 32%, advantageously at least 33%, advantageously at least 34%, advantageously at least 35%, advantageously at least 36%, advantageously at least 37%, advantageously at least 38%, advantageously at least 39%, advantageously at least 40%, advantageously at least 41%, advantageously at least 42%, advantageously at least 43%, advantageously at least 44%, advantageously at least 45%, advantageously at least 46%, advantageously at least 47%, advantageously at least 48%, advantageously at least 49%, advantageously at least 50%, advantageously at least 51%, advantageously at least 52%, advantageously at least 53%, advantageously at least 54%, advantageously at least 55%, advantageously at least 56%, advantageously at least 57%, advantageously at least 58%, advantageously at least 59%, advantageously at least 60%, advantageously at least 61%, advantageously at least 62%, advantageously at least 63%, advantageously at least 64%, advantageously at least 65%, advantageously at least 66%, advantageously at least 67%, advantageously at least 68%, advantageously at least 69%, advantageously at least 70%, advantageously at least 71%, advantageously at least 72%, advantageously at least 73%, advantageously at least 74%, advantageously at least 75%, advantageously at least 76%, advantageously at least 77%, advantageously at least 78%, advantageously at least 79%, advantageously at least 80%, advantageously at least 81%, advantageously at least 82%, advantageously at least 83%, advantageously at least 84%, advantageously at least 85%, advantageously at least 86%, advantageously at least 87%, advantageously at least 88%, advantageously at least 89%, advantageously at least 90%, advantageously at least 91%, advantageously at least 92%, advantageously at least 93%, advantageously at least 94%, advantageously at least 95%, advantageously at least 96%, advantageously at least 97%, advantageously at least 98%, advantageously at least 99%, advantageously 100% of the total volume of said suspension.

In another embodiment of step e) according to the method of the invention, when transferring at least a portion of the suspension obtained in step d) from at least one mixing vessel to the n culture vessels, the fraction of the volume of homogenized suspension of mixed living cells transferred to each of the n culture vessels may be the same or different.

By way of example, if four culture vessels are used, in transfer step e), it is possible to allocate a fraction of 25% of the total volume of the homogenized suspension of mixed cells to each of the four culture vessels.

By way of example, if four culture vessels are used, in the transfer step e) it is possible to transfer 10% of the total volume of the homogenized suspension of living cells contained in the mixing vessel to the first culture vessel, 20% of the same volume to the second culture vessel, 30% of the same volume to the third culture vessel and 5% of the same volume to the fourth culture vessel.

By way of example, if four culture vessels are used, in the transfer step e) it is possible to transfer 0% of the total volume of the homogenized suspension of living cells contained in the mixing vessel to the first culture vessel, 20% of the same volume to the second culture vessel, 30% of the same volume to the third culture vessel and 5% of the same volume to the fourth culture vessel.

The above examples are not limiting and serve only to illustrate step e).

Step f) of the method consists of repeating steps b) to e). For the purposes of the present invention, a "culture cycle" means the repetition of steps b) to e) of the method.

In a particular embodiment of the invention, when repeating step b), the selective regime and/or culture parameters used in a culture cycle may be the same or different from those used in the preceding culture cycle. Advantageously, the selective regime and/or the culture parameters used can be the same or different from one culture cycle to another.

In a particular embodiment of the invention, the selective regime, chosen for each culture vessel, may be the same or different from one culture cycle to another. Advantageously, the selective regime is selected from the group comprising chemostat, turbidostat, medium swap, and iterated batch, the list being non-limiting.

In a particularly advantageous embodiment of the invention, the selective regime in a given culture vessel may be identical from one cycle to another. By way of example, it is possible to apply, in a given culture vessel, a chemostat selective regime during a culture cycle, and then apply, in the same culture vessel, that same culture regime for the next culture cycle. By way of example, it is possible to apply, in a given culture vessel, a turbidostat selective regime during a culture cycle, and then apply, in the same culture vessel, that same culture regime for the next culture cycle. The examples described above are not limiting and apply to all selective culture regimes.

In another particularly advantageous embodiment of the invention, the selective regime in a given culture vessel may be modified from one cycle to another. As an example, it is possible to apply, in a given culture vessel, a chemostat selective regime during one culture cycle, and then to change the selective culture regime, for that same culture vessel, to a turbidostat selective regime for the next culture cycle. As an example, it is possible to apply, in a given culture vessel, a chemostat selective regime during one culture cycle, and then to change the selective culture regime, for that same culture vessel, to a turbidostat selective regime for the next culture cycle, then to change the selective culture regime, for that same culture vessel, to a chemostat selective regime for the next culture cycle. As an example, it is possible to apply, in a given culture vessel, a chemostat selective regime during one culture cycle, and then to change the selective culture regime, for that same culture vessel, to a turbidostat selective regime for the next culture cycle, then to change the selective culture regime, for that same culture vessel, to a medium swap selective regime for the next culture cycle. The examples described above are not limiting and apply to all selective culture regimes.

In a particular embodiment of the invention, when repeating step b), the culture parameters used may be, for each culture vessel, the same or different from one culture cycle to another. Advantageously, the culture parameters are selected from the group consisting of dilution rate, temperature, pH, composition of the culture medium(s), composition of the gas stream and one of the combinations thereof, said parameters potentially being identical from one cycle to another. Advantageously, the culture parameters are selected from the group consisting of dilution rate, temperature, pH, composition of the culture medium(s), composition of the gas stream and one of the combinations thereof, said parameters potentially being modified from one cycle to another. Advantageously, it is possible to modify only one of these culture parameters, that is to modify only the temperature or to modify only the pH or to modify only the composition of the culture medium, or to modify only the composition of the gas stream. Advantageously, it is possible to simultaneously modify several of these culture parameters. Advantageously, it is possible to simultaneously modify at least two culture parameters, at least three culture parameters, at least four culture parameters.

In a particularly advantageous embodiment according to the invention, in the second culture cycle, the initial temperature T0i of each culture vessel RCi may be increased by a value ΔT relative to the first culture cycle, and then, in each new culture cycle, may undergo a temperature increment of ΔT per culture cycle. Advantageously, the value ΔT is 0.1° C., advantageously 0.2° C., advantageously 0.3° C., advantageously 0.4° C., advantageously 0.5° C., advantageously 0.6° C., advantageously 0.7° C., advantageously 0.8° C., advantageously 0.9° C., advantageously 1.0° C., advantageously 1.1° C., advantageously 1.2° C., advantageously 1.3° C., advantageously 1.4° C., advantageously 1.5° C., advantageously 1.6° C., advantageously 1.7° C., advantageously 1.8° C., advantageously 1.9° C., advantageously 2.0° C., advantageously 2.1° C., advantageously 2.2° C., advantageously 2.3° C., advantageously 2.4° C., advantageously 2.5° C., advantageously 2.6° C., advantageously 2.7° C., advantageously 2.8° C., advantageously 2.9° C., advantageously 3.0° C., advantageously 3.1° C., advantageously 3.2° C., advantageously 3.3° C., advantageously 3.4° C., advantageously 3.5° C., advantageously 3.6° C., advantageously 3.7° C., advantageously 3.8° C., advantageously 3.9° C., advantageously 4.0° C. Advantageously, the value of ΔT may be the same or different at each new cycle.

In a particularly advantageous embodiment according to the invention, in the second culture cycle, the initial temperature T0i of each culture vessel RCi may be decreased by a value ΔT relative to the first culture cycle, and then, in each new culture cycle, may undergo a temperature decrement of ΔT per culture cycle. Advantageously, the value ΔT is −0.1° C., advantageously −0.2° C., advantageously −0.3° C., advantageously −0.4° C., advantageously −0.5° C., advantageously −0.6° C., advantageously −0.7° C., advantageously −0.8° C., advantageously −0.9° C., advantageously 1.0° C., advantageously −1.1° C., advantageously −1.2° C., advantageously −1.3° C., advantageously −1.4° C., advantageously −1.5° C., advantageously −1.6° C., advantageously −1.7° C., advantageously −1.8° C., advantageously −1.9° C., advantageously −2.0° C., advantageously −2.1° C., advantageously −2.2° C., advantageously −2.3° C., advantageously −2.4° C., advantageously −2.5° C., advantageously −2.6° C., advantageously −2.7° C., advantageously −2.8° C., advantageously −2.9° C., advantageously −3.0° C., advantageously −3.1° C., advantageously −3.2° C., advantageously −3.3° C., advantageously −3.4° C., advantageously −3.5° C., advantageously −3.6° C., advantageously −3.7° C., advantageously −3.8° C., advantageously −3.9° C., advantageously −4.0° C. Advantageously, the value of ΔT may be the same or different at each new cycle.

In another particularly advantageous embodiment according to the invention, in the second culture cycle, the initial pH pH(i,k) may be increased by a value ΔpH relative to the first culture cycle, then, in each new culture cycle, may undergo a temperature increment of ΔpH per culture cycle. Advantageously, the value ΔpH is 0.1 pH unit, advantageously 0.2 pH unit, advantageously 0.3 pH unit, advantageously 0.4 pH unit, advantageously 0.5 pH unit. Advantageously, the value of ΔpH can be the same or different at each new cycle.

In another particularly advantageous embodiment according to the invention, in the second culture cycle, the initial pH pH(i,k) may be decreased by a value ΔpH relative to the first culture cycle, then, in each new culture cycle, may undergo a temperature decrement of ΔpH per culture cycle. Advantageously, the value ΔpH is −0.1 pH unit, advantageously −0.2 pH unit, advantageously −0.3 pH unit, advantageously −0.4 pH unit, advantageously −0.5 pH unit. Advantageously, the value of ΔpH can be the same or different at each new cycle.

In another particularly advantageous embodiment according to the invention, in the second culture cycle, the composition of the initial culture medium MC(i,k) or of the culture media MC(i,k)-permissive and MC(i,k)-stressing, can be changed, for each of the culture vessels RCi, relative to the first culture cycle, then undergo a further change at each new culture cycle. Advantageously, the modification of the composition of the culture medium or media may consist of an increase in the content of toxic agent, such as growth inhibitors. Advantageously, the modification of the composition of the culture medium may consist of a decrease in the content of a growth factor essential for cell growth. Advantageously, the modification of the composition of the culture medium may consist of a replacement of one substrate with another. Advantageously, the modification of the composition of the culture medium may consist of a replacement of a permissive culture medium with a stressing culture medium. Advantageously, the modification of the composition of the culture medium may consist of a replacement of a rich medium with a minimal medium. Advantageously, the modification of the composition of the culture medium may consist of a replacement of a minimal medium with a rich medium. Advantageously, the modification of the composition of the culture medium may consist of a replacement of a synthesis medium (also called defined medium) with a complex medium (also called undefined medium). Advantageously, the modification of the composition of the culture medium may consist of a replacement of a complex medium (also called undefined medium) with a synthesis medium (also called defined medium). Advantageously, the composition of the culture medium can be the same or different for each new cycle.

In a particularly advantageous embodiment according to the invention, in the second culture cycle, the dilution rate Td(i,k) of each culture vessel RCi may be increased by a value ΔTd relative to the first culture cycle, then, in each new culture cycle, may undergo an increment of ΔTd. Advantageously, the value ΔTd is 0.01 $h^{-1}$, advantageously 0.02 $h^{-1}$, advantageously 0.03 $h^{-1}$, advantageously 0.04 $h^{-1}$, advantageously 0.05 $h^{-1}$, advantageously 0.06 $h^{-1}$, advantageously 0.07 $h^{-1}$, advantageously 0.08 $h^{-1}$, advantageously 0.09 $h^{-1}$, advantageously 0.10 $h^{-1}$, advantageously 0.15 $h^{-1}$, advantageously 0.20 $h^{-1}$, advantageously 0.25 $h^{-1}$, advantageously 0.30 $h^{-1}$, advantageously 0.35 $h^{-1}$, advantageously 0.40 $h^{-1}$, advantageously 0.45 $h^{-1}$, advantageously 0.50 $h^{-1}$, advantageously 0.55 $h^{-1}$, advantageously 0.60 $h^{-1}$, advantageously 0.65 $h^{-1}$, advantageously 0.70 $h^{-1}$, advantageously 0.75 $h^{-1}$, advantageously 0.80 $h^{-1}$, advantageously 0.85 $h^{-1}$, advantageously 0.90 $h^{-1}$, advantageously 0.95 $h^{-1}$, advantageously 1.00 $h^{-1}$, advantageously 1.05 $h^{-1}$, advantageously 1.10 $h^{-1}$, advantageously 1.15 $h^{-1}$, advantageously 1.20 $h^{-1}$, advantageously 1.25 $h^{-1}$, advantageously 1.30 $h^{-1}$, advantageously 1.35 $h^{-1}$, advantageously 1.40 $h^{-1}$, advantageously 1.45 $h^{-1}$, advantageously 1.50 $h^{-1}$. Advantageously, the value of ΔTd can be the same or different at each new cycle.

In another particularly advantageous embodiment according to the invention, during the second culture cycle, the composition of the initial gas stream Gi of each of the culture vessels RCi can be modified with respect to the first culture cycle, and then at each new culture cycle, undergo another modification of the gas stream composition. Advantageously, the modification of the composition of the gas stream may consist in an increase or a decrease of the content of one or several gases constituting the flow, the gas being chosen among air, nitrogen ($N_2$), carbon monoxide (CO), carbon dioxide ($CO_2$), methane ($CH_4$), hydrogen sulfide ($H_2S$), oxygen ($O_2$), nitrous oxide ($N_2O$), dihydrogen ($H_2$), or a combination thereof. Advantageously, the composition of the gas stream can be the same or different for each new cycle.

In another particularly advantageous embodiment according to the invention, in the second culture cycle, the suspensions in each culture vessel RCi may be maintained at a temperature T0+ΔT and a pH pHk+ΔpH for one culture cycle, then in each new culture cycle, may undergo a temperature increment of ΔT and a pH increment of ΔpH for each of the n culture vessels per culture cycle.

The examples described above are not limiting and apply equally to the modification of a single culture parameter or the simultaneous modification of several culture parameters.

In a particular embodiment of the invention, when repeating step b), the selective regime and/or the culture parameters used may be modified from one culture cycle to another, said modification being applicable to all n culture vessels. Whatever modification is made, it is applicable to all n culture vessels.

In another particular embodiment of the invention, when repeating step b), the selective regime and/or the culture parameters used may be modified from one culture cycle to another said modification not being applicable to all n culture vessels.

In another particular embodiment of the invention, when repeating step b), the selective regime may be modified from one culture cycle to another, said modification not being applicable to all n culture vessels.

By way of example, in step b), culture vessel RC1 can be subjected to a chemostat selective regime and the remaining n−1 culture vessels can be subjected to a turbidostat selective regime for one culture cycle, then at each new culture cycle, undergo a modification of the selective regime.

By way of example, in step b), culture vessel RC1 may be subjected to a chemostat selective regime, culture vessel RC2 may be subjected to a turbidostat selective regime, and the remaining n−2 culture vessels may be subjected to a medium swap selective regime for one culture cycle, and then at each new culture cycle undergo a modification of the selective regime.

The examples described above are not limiting and apply to all selective culture regimes.

In a particularly advantageous embodiment of the invention, when repeating step b), the culture parameters used may be modified from one culture cycle to another, said modification not being applicable to all n culture vessels.

By way of example, in step b), culture vessel RC1 can be maintained at a temperature T0+0.1° C. and the remaining n−1 culture vessels can be maintained at the initial temperature T0, for one culture cycle, then at each new culture cycle, undergo a temperature increment of 0.1° C. for each of the n culture vessels per culture cycle. In this case, during the second cycle, culture vessel RC1 would be maintained at a temperature T0+0.2° C. and the remaining n−1 culture vessels would be maintained at a temperature T0+0.1° C., and so on.

According to another example, in step b), culture vessel RC1 can be maintained at a temperature T0+0.2° C., culture vessel RC2 can be maintained at a temperature T0+0.10° C., and the remaining n−2 culture vessels can be maintained at the initial temperature T0, for one culture cycle, then, at each new culture cycle, undergo a temperature increment of 0.1° C. for each of the n culture vessels per culture cycle. In this case, in the second cycle, culture vessel RC1 would be maintained at a temperature of T0+0.3° C., culture vessel RC2 would be maintained at a temperature of T0+0.2° C. and the remaining n−2 culture vessels would be maintained at a temperature of T0+0.1° C., and so on.

The examples described above are not limiting and apply equally to the modification of a single culture parameter and to the simultaneous modification of several culture parameters.

In a particular embodiment of the invention, steps b) to e) are repeated as many times as necessary, until the appearance of a living cell that has acquired a phenotype of interest.

In a particular embodiment of the invention, the selective regime and/or culture parameters can be adapted automatically in response to observable/measurable criteria on the cultures in the preceding cycle. For example, a selective pressure criterion such as temperature or the concentration of a cell growth inhibiting molecule may have its value modified for the current cycle if the cell growth rate is below/above a certain predefined threshold during the preceding cycle. Or, after several cycles of evolution to adapt the suspension of living cells to a target concentration of inhibitor molecule (medium swap mode), the culture parameters can be modified to increase the growth rate of the cells (turbidostat mode).

Step g) of the method consists of collecting, after several culture cycles in at least one of the n culture vessels, the living cells that have acquired a phenotype of interest.

Advantageously, the phenotype of interest is acquired by evolutionary adaptation, in particular by the accumulation over several generations of beneficial mutations by the living cell, the beneficial mutations being able to be spontaneous, or not spontaneous, for example following exposure to ultraviolet rays, following exposure to one or more mutagenic agents, or following genetic modifications leading to a mutation rate higher than the natural mutation rate of the organism.

In a particular embodiment of the invention, the collection step g) is performed using harvesting means, which may be selected from a sterile syringe, a sterile micropipette, or any other means for sampling living cells that have acquired a phenotype of interest.

Advantageously, the living cells that have acquired a phenotype of interest are collected after 2 cycles, advantageously after 3 cycles, advantageously after 4 cycles, advantageously after 5 cycles, advantageously after 6 cycles, advantageously after 7 cycles, advantageously after 8 cycles, advantageously after 9 cycles, advantageously after 10 cycles, advantageously after 20 cycles, advantageously after 30 cycles, advantageously after 40 cycles, advantageously after 50 cycles, advantageously after 60 cycles, advantageously after 70 cycles, advantageously after 80 cycles, advantageously after 90 cycles, advantageously after 100 cycles, advantageously after 150 cycles, advantageously after 200 cycles, advantageously after 250 cycles, advantageously after 300 cycles, advantageously after 350 cycles, advantageously after 400 cycles, advantageously after 450 cycles, advantageously after 500 cycles, advantageously after 550 cycles, advantageously after 600 cycles, advantageously after 650 cycles, advantageously after 700 cycles, advantageously after 750 cycles, advantageously after 800 cycles, advantageously after 850 cycles, advantageously after 900 cycles, advantageously after 950 cycles, advantageously after 1000 cycles, advantageously after 5000 cycles, advantageously after 10,000 cycles, advantageously after 15,000 cycles, advantageously after 20,000 cycles, advantageously after 25,000 cycles, advantageously after 30,000 cycles, advantageously after 35,000 cycles, advantageously after 40,000 cycles, advantageously after 45,000 cycles, advantageously after 50,000 culture cycles.

In a particular embodiment of the invention, the method may further optionally comprise at least one step of sterilizing the n culture vessels and the at least one mixing vessel. Advantageously, the at least one sterilization step is implemented as soon as at least one culture vessel and/or at least one mixing vessel is empty. Advantageously, the at least one sterilization step is implemented after step c) for the culture vessel. Advantageously, the at least one sterilization step is implemented after step e) for the at least one mixing vessel. In one particular embodiment, the at least one sterilization step is carried out by adding a sterilizing solution, chosen from among a solution containing a weak base such as ammonia, a solution containing a strong base such as lye (NaOH) or potash (KOH), a solution containing a strong acid such as sulfuric acid, hydrochloric acid, a solution containing a weak acid such as acetic acid, a solution containing an oxidizing agent such as hydrogen peroxide and sodium hypochlorite, a solvent such as ethanol and isopropanol, or a combination thereof. Advantageously, in the case of a combination of the above solutions, the solutions can be used simultaneously or successively, that is one after the other. Advantageously, the sterilizing solution is a lye solution, preferably a lye solution of at least 0.1 M and even more preferentially more than 1 M. Advantageously, the sterilization step can be performed as described, for example, in patent EP1135460, that is by temporarily transferring the entire volume of suspension of living cells from a culture or mixing vessel to a storage vessel and then contacting the entire inner surface of the culture or mixing vessel with sterilizing solution(s), followed by a rinse solution. The suspension of living cells is then transferred back to the now-sterilized initial culture or mixing vessel.

Advantageously, the sterilization step makes it possible, on the one hand, to eliminate biofilms and, on the other hand, to return the at least one culture vessel and the at least one mixing vessel to nominal sterile conditions, according to their respective initial state.

In a particular embodiment of the invention, the method may further optionally comprise at least one step of cleaning the n culture vessels and the at least one mixing vessel. Advantageously, the at least one cleaning step is carried out after the at least one sterilization step. In a particular embodiment, the at least one cleaning step is performed by adding a cleaning solution making it possible to neutralize the sterilizing agent. Advantageously, the cleaning solution is selected from acidic solutions, such as acetic or sulfuric acid solutions and detergent solutions, in particular solutions containing surfactants.

In a particular embodiment of the invention, the method may further optionally comprise at least one step of rinsing the n culture vessels and the at least one mixing vessel. Advantageously, the at least one rinsing step is carried out after the at least one cleaning step. In a particular embodiment, the at least one rinsing step is performed by adding a rinsing solution making it possible to remove cleaning solution residue. Advantageously, the rinsing solution is water, preferentially sterile water.

In a particular embodiment of the invention, the method may further optionally comprise at least one step of exposure to ultraviolet light and/or a step of exposure to a mutagenic agent. Advantageously, the step of exposure to ultraviolet light and/or the step of exposure to a mutagenic agent can be implemented at any point in the method of the invention. In a particularly advantageous embodiment of the invention, the step of exposure to ultraviolet light is implemented between steps c) and d) of the method according to the invention or between steps d) and e) of the method according to the invention.

In another particularly advantageous embodiment of the invention, the step of exposure to a mutagenic agent is implemented between steps c) and d) of the method according to the invention or between steps d) and e) of the method according to the invention. Advantageously, the mutagenic agent may be selected from alkylating agents, such as N-nitroso-N-ethylurea (also referred to as N-ethyl-N-nitrosourea (ENU)) or ethyl methanesulfonate (also referred to as ethyl methanesulfonate (EMS)), intercalating agents, such as proflavin and acridine orange, and reactive oxygen species, especially free radicals, oxygen ions, and peroxides.

The method according to the present invention can be implemented in a device for continuous culture of living cells for the evolutionary adaptation of said living cells, said device comprising:

- n culture vessels, each culture vessel being arranged to receive a culture medium and living cells,
- at least one mixing vessel and
- at least one sterile fluid supply unit comprising at least one culture medium reservoir, the sterile fluid supply unit being connected to the n culture vessels and the at least one mixing vessel via a main supply line.

Advantageously, the circulation of the fluids in the sterile fluid supply unit, namely the circulation of the gas, the circulation of the sterilizing, cleaning and rinsing solutions, and the circulation of the culture media, is achieved through the use of pumps and valves. The pumps and valves can be, for example, operated mechanically and can be controlled electrically or electronically, advantageously automatically using control means which are not shown.

In a particular embodiment, the sterile fluid supply unit comprises at least one external gas source, at least one sterilizing solution reservoir, at least one cleaning solution reservoir, at least one rinsing solution reservoir, and at least one culture medium reservoir. In a particular embodiment, the sterile fluid supply unit further comprises a harvesting means, advantageously a syringe, making it possible to introduce the living cells into each of n culture vessels and to collect the living cells that have acquired a phenotype of interest. In an alternative embodiment, living cells that have acquired a phenotype of interest are collected by means of a fluid connection to another analysis device.

Advantageously, each of the n culture vessels may further comprise at least one gas supply device. The at least one gas supply device allows the injection of a pressurized gas stream into the culture vessel, allowing the supply of gas required for the growth of the suspension and the homogenization of said suspension (bubbling agitation). Advantageously, the at least one gas supply device allows the injection of a pressurized gas stream into the culture vessel, known as the transfer stream, which makes it possible to increase the pressure in said culture vessel and thus to push the suspension, such as a syringe plunger, towards the mixing vessel.

Alternatively, in addition to the at least one gas supply device, each of the n culture vessels may further comprise at least one transfer gas supply device. In this case, the transfer stream comes solely and directly from the at least one transfer gas supply device, and the aeration and agitation flow comes solely from the at least one gas supply device. The use of a transfer gas increases the pressure in said culture vessel and thus pushes the suspension, like a syringe plunger, towards the mixing vessel.

Advantageously, each of the n culture vessels may further comprise at least one supply line. The at least one supply line allows the culture vessel to be filled with culture medium from at least one culture medium reservoir and the culture vessel to be filled with sterilization, cleaning, and rinsing solutions from the corresponding reservoirs.

The supply line also allows the transfer of all or part of the suspension from the culture vessel to a mixing vessel by pressurizing said culture vessel and emptying the culture vessel. The at least one supply line also allows for the filling of the culture vessel when transferring all or a portion of the suspension from the mixing vessel to the at least one culture vessel. The supply line also allows the contents of the culture vessel to be emptied into a waste bin during the sterilization, cleaning and rinsing operations.

A supply valve controls access to the supply line to allow the filling or emptying of the culture vessel.

Advantageously, each of the n culture vessels may further comprise at least one discharge device allowing the evacuation of bubbling gases during the culture, as well as the evacuation of gases, culture medium or media, and the sterilization, cleaning and rinsing solutions during the filling operations of the culture vessel. Advantageously, the discharge device is controlled via a discharge valve.

Advantageously, each of the n culture vessels may further comprise at least one leveling line. The at least one leveling line allows the volume of the suspension in the culture vessel to be controlled. Advantageously, a leveling valve controls access to the leveling line. Advantageously, the leveling line is located at a height less than or equal to half the total height of the culture vessel from the bottom of said vessel.

Even more advantageously, each of the n culture vessels may further comprise:

at least one gas supply device,
at least one discharge device,
at least one leveling line, and
at least one supply line.

In a particular embodiment, each of the n culture vessels comprises:

at least one gas supply device in the lower part of the culture vessel,
at least one discharge device in the upper part of the culture vessel,
at least one leveling line at a height less than or equal to half the total height of the culture vessel from the bottom of said culture vessel, and,
at least one supply line in the lower part of the culture vessel.

Advantageously, the culture vessels are closed culture vessels. Culture vessels can be disposable or reusable. Particularly advantageous is the fact that the culture vessels are reusable.

In a particular embodiment, each of the n culture vessels comprises living cells in a culture medium. Advantageously, no culture vessel of the device is empty.

In a particular embodiment, the culture device comprises a single sterile fluid supply unit for all n culture vessels and the at least one mixing vessel.

In another particular embodiment, the culture device comprises a sterile fluid supply unit per culture vessel. Advantageously, each of the n culture vessels is connected individually, and independently of each other, to a sterile fluid supply unit. The sterile fluid supply unit is connected to its culture vessel via a supply valve.

In a particular embodiment of the invention, the at least one mixing vessel is a culture vessel arranged to receive the contents of at least two culture vessels.

In another particular embodiment of the invention, the at least one mixing vessel is a single vessel, independent of the set of n culture vessels, and is arranged to receive the contents of the set of n culture vessels.

Advantageously, when the mixing vessel is a single vessel, independent of the set of culture vessels, said mixing vessel comprises:

a gas supply device in the upper part of said mixing vessel,
a discharge device in the upper par of said mixing vessel,
a supply line in the lower part of said mixing vessel.

Advantageously, the mixing vessel is a closed culture vessel. The mixing vessel can be disposable or reusable. Particularly advantageously, the mixing vessel is a reusable vessel.

In a particular embodiment, the mixing vessel comprises an agitation means, advantageously a mechanical agitator or by gas injection.

In a particular embodiment, the culture device further comprises a control unit, arranged and configured to actuate all the different supply means, in particular the pumps and valves; allowing the transfer of the contents of at least one culture vessel to the at least one mixing vessel and vice versa.

Advantageously, the culture device is controlled by the control unit.

In a particular embodiment, the culture device further comprises a control unit, arranged and configured to measure physical/chemical indicators, including cell density, in each of the culture vessels, measure the growth dynamics of the suspension, and control the automatic triggering of suspension mixtures in the n mixing vessels.

FIGURES

FIG. 1*a* represents a device for continuous culture of living cells according to a particular embodiment of the invention, the device comprising a sterile fluid supply unit and three culture vessels, all of the culture vessels being arranged to be respectively and successively a mixing vessel, one mixing vessel being arranged to receive the contents of at least two culture vessels.

FIG. 1*b* represents a device according to FIG. 1*a* and shows step c) of the method according to a particular embodiment of the invention wherein the entire suspension from a first culture vessel is transferred to a second culture vessel which becomes a mixing vessel.

FIG. 1*c* represents a device according to FIG. 1*a* and shows step e) of the method according to a particular embodiment of the invention wherein at least a fraction of the suspension obtained in step d) in the second culture vessel is transferred to the first culture vessel.

FIG. 2*a* represents a device for continuous culture of living cells according to a second embodiment, wherein the device comprises a single mixing vessel, independent of the set of n culture vessels, and is arranged to receive the contents of the set of n culture vessels.

FIG. 2*b* represents a device according to FIG. 2*a* and shows step c) of the method according to a particular embodiment of the invention wherein the entire suspension from the n culture vessels is transferred to the mixing vessel.

FIG. 2*c* represents a device according to FIG. 2*a* and shows step e) of the method according to a particular embodiment of the invention wherein at least a fraction of the suspension obtained in step d) from the mixing vessel is transferred to each of the n culture vessels.

FIG. 3 represents a device for continuous culture of living cells according to a third embodiment, wherein the device comprises four culture vessels, each of the culture vessels being connected individually, and independently of each other, to a sterile fluid supply unit, and wherein the four culture vessels are arranged so that they can be respectively and successively a mixing vessel, one mixing vessel being arranged to receive the contents of at least two culture vessels.

FIG. 4 represents a device for continuous culture of living cells according to a fourth embodiment, wherein the device comprises four culture vessels, each of the culture vessels being connected individually, and independently of each other, to a sterile fluid supply unit, and a single mixing vessel, independent of the set of 4 culture vessels, said mixing vessel being arranged to receive the contents of the set of 4 culture vessels.

FIG. 5 represents the evolution of a bacterial strain of the Pseudomonadacea family. In this figure, the total number of dilutions triggered each day is plotted against the number of days FIG. 6 represents the adaptation of the bacterial strain of the Pseudomonadacea family at 30° C. by plotting the change in the temperature in each of the culture vessels RC1 and RC2 against the number of culture cycles.

FIG. 7 represents the adaptation of the bacterial strain of the Pseudomonadacea family at 30° C. by plotting the change in the temperature in each of the culture vessels RC1 and RC2 against the number of days of the experiment.

FIG. 8 represents the dilution rate adaptation of a bacterial strain of the Pseudomonadacea family grown at 25° C. either in a single 15 mL culture vessel (solid squares) or in a single 80 mL culture vessel (solid rounds) according to a method not in accordance with the invention. In this figure the dilution rate in $hour^{-1}$ is a function of the number of days.

FIG. 9 shows the adaptive evolution at a temperature of 25° C. with a forced dilution rate of 0.2 $hours^{-1}$ of a bacterial strain of the Pseudomonadacea family cultured with successive combination and separation of the suspensions between 2 15 mL culture vessels (RC1: solid diamonds; RC2: solid triangles) according to the method in accordance with the invention. In this figure the temperature (° C.) is a function of the number of days.

DETAILED DESCRIPTION

The design and functionality of the device for continuous culture of living cells for the evolutionary adaptation of said living cells are described in FIGS. 1*a* to 4.

The device for continuous cell culture of living cells, as shown in FIGS. 1*a* to 2*c*, comprises three culture vessels, a first culture vessel RC1, a second culture vessel RC2 and a third culture vessel RC3. The first culture vessel RC1 is adjacent to the second culture vessel RC2, which is adjacent to the third culture vessel RC3. The culture vessels are arranged to contain living cells and culture media, and allow the culture of said cells.

With reference to FIG. 1*a*, the culture device includes a sterile fluid supply unit 10 comprising an external gas source GS, a sterilizing solution reservoir AS, a cleaning solution reservoir AC, a rinsing solution reservoir AR, and three culture medium reservoirs M1, M2 and M3. The circulation of the fluids in the sterile fluid supply unit 10, namely the circulation of the gas, the circulation of the sterilizing, cleaning and rinsing solutions, and the circulation of the culture media, is achieved through the use of pumps and valves. The pumps and valves can be operated mechanically, for example, and can be controlled electrically and/or electronically, advantageously automatically using control means which are not shown. The sterile fluid supply unit 10 further comprises a harvesting means, advantageously a syringe 11, for introducing cells into the culture vessels and for sampling living cells that have acquired a phenotype of interest. For simplicity's sake, in FIGS. 1*b*, 1*c*, 2*a*, 2*b*, 2*c*, 3, and 4 the sterile fluid supply unit 10 is shown as a block or square.

With reference to FIGS. 1*a*, 1*b*, 1*c*, 2*a*, 2*b*, 2*c*, the culture device comprises a main supply line C10 and supply valves 1, 2, 3, Va1, Va2 and Va3 connected to the main supply line C10. Said supply line C10 and said valves are located at the bottom of the culture vessels. The sterile fluid supply unit 10 is connected to the three culture vessels via said supply line C10 and said valves. They allow the filling of gas, sterilizing solution, cleaning and rinsing solution, culture media and living cells into the culture vessels. They also allow the transfer of the contents of the culture vessels, for example when transferring all or part of the suspension from the mixing vessel to a culture vessel and allow the emptying of the culture vessel when transferring all or part of the suspension from the culture vessel to the mixing vessel. The supply valve Va1 allows the culture vessel RC1 to be filled or emptied. The supply valve Va2 allows the culture vessel RC2 to be filled or emptied. The supply valve Va3 allows the culture vessel RC3 to be filled or emptied. Valves 1, 2, 3, Va1, Va2 and Va3 are normally closed in the inactive state. When the supply valve Vai is in the open position, the culture vessel RCi can be filled or emptied. When the supply valve Vai is in the closed position, it is not possible to fill or empty the culture vessel RCi.

The culture device comprises three gas supply devices G1, G2 and G3. Each culture vessel RC1, RC2 and RC3 is connected to a gas supply device G1, G2 or G3 which makes it possible to inject a pressurized gas stream into the culture vessel, inject gas into the suspension, homogenize said suspension (bubbling agitation), and pressurize the culture vessel as needed. Each gas supply device G1, G2 or G3 is connected to the culture vessel from its lower part by means of a gas supply line CG opening into the culture vessel at a height of about one-quarter of the total height of the vessel from the bottom of said vessel.

The culture device comprises three discharge devices W1, W2 and W3. Each culture vessel RC1, RC2 and RC3 is connected to a discharge device W1, W2 or W3 making it possible to evacuate the gases injected into the suspension during the culture, as well as the evacuation of the gases, from the culture medium/media and the sterilization, cleaning and rinsing solutions during the filling operations of the culture vessel. The discharge device is located in the upper part of the culture vessel. The culture device comprises three discharge valves Vd1, Vd2 and Vd3. Each culture vessel RC1, RC2 and RC3 is connected to a discharge valve Vd1, Vd2 and Vd3, respectively, so as to control the discharge of the gases injected during the culture, as well as the discharge of the gases, from the culture medium/media and the sterilization solution AS, cleaning solution AC and rinsing solution AR during the filling operations of the culture vessel. The discharge valves Vd1, Vd2 and Vd3 are normally in the open position in the inactive state. When the discharge valve is in the open position, the culture vessel can be filled. When the discharge valve is in the closed position, the transfer of all or part of the suspension contained in the culture vessel to the mixing vessel can be done by pressurizing said culture vessel.

With reference to FIGS. 1*a*, 1*b*, 1*c*, the culture device comprises three leveling valves Vt1, Vt2 and Vt3. Each culture vessel RC1, RC2 and RC3 is connected to a leveling valve Vt1, Vt2 and Vt3 respectively via a leveling line CT. Each leveling line CT opens into a culture vessel at a height less than or equal to half the total height of the culture vessel from the lower part of said vessel. Each leveling valve Vt1, Vt2 and Vt3 is also connected to the main line C10. Each leveling valve controls the volume contained in each of the culture vessels, so that the volume remains constant when culture medium is added. The leveling valves Vt1, Vt2 and Vt3 are normally in the closed position in the inactive state. When the leveling valve is in the open position, a volume of suspension in excess of the suspension volume defined by the position of the leveling line is discharged from the culture vessel to the supply line C10.

FIGS. 1*a*, 1*b* and 1*c* represent a first particular embodiment wherein the three culture vessels are arranged to respectively and successively become a mixing vessel during the cell culture method.

The method for continuous cell culture of living cells associated with the culture device shown in FIGS. 1*a*, 1*b* and 1*c* will now be described.

According to FIG. 1*a*, each of the three culture vessels RC1, RC2, and RC3 comprises living cells in a culture medium. Each culture vessel RC1, RC2 and RC3 is filled to about half its capacity. The living cells are cultured according to a given selective regime, using defined culture parameters, until they reach a given growth stage, in order to obtain a suspension of living cells in each of the three culture vessels. For this purpose, a pressurized gas stream is injected into each of the three culture vessels via the gas supply device G1, G2 or G3 respectively, allowing the injection of gas and the homogenization of the suspension (bubbling agitation) inside each of the three culture vessels. Valves 1, 2, 3, 4, the leveling valves Vt1, Vt2 and Vt3, and the supply valves Va1, Va2 and Va3 are in the closed position. Only the discharge valves Vd1, Vd2 and Vd3 are in the open position.

Next, FIG. 1*b* represents step c) of the method according to the invention consisting of transferring the entire suspension obtained in step b) from at least one culture vessel (RCi) to the at least one mixing vessel and step d) consisting of mixing the suspension in step c) in the at least one mixing vessel.

According to FIG. 1*b*, all of the suspension in culture vessel RC1 is transferred to culture vessel RC2, as shown by arrow f12. The supply valves Va1, 2, Va2 are in the active position (in black in FIG. 1*b*) and therefore open, so that the suspension from the first vessel RC1 passes through said valves to the second culture vessel RC2. The discharge valve Vd1 of the first vessel is in the active position (black in FIG. 1*b*) and therefore closed, so as to pressurize the first culture vessel. The discharge valve Vd2 of the second vessel remains in the inactive and thus open position, so as to allow filling into the second culture vessel RC2. In order to allow the culture vessel RC1 to be emptied, the gas supply device G1 injects a pressurized gas stream, known as the transfer stream, via the gas supply line CG, which makes it possible to increase the pressure in the culture vessel RC1 and thus pushes the suspension like a syringe plunger. The culture vessel RC2 then becomes the mixing vessel and comprises both the suspension initially contained in the second culture vessel RC2 and the suspension from the first culture vessel RC1.

In a manner not illustrated, a pressurized gas stream is injected into the second culture vessel RC2 allowing, via the gas supply device G2, the gas injection of the suspension and the homogenization of the cell suspension (bubbling agitation) inside the culture vessel RC2.

Regarding the third culture vessel RC3, the culture step is maintained by injecting pressurized gas stream into the culture vessel RC3 and by keeping the valve Vd3 open.

Regarding culture vessel RC1, the sterilization, cleaning and rinsing steps are carried out by opening the valves 1, Va1. First, the sterilization step is started by adding a sterilizing solution from the sterilizing solution reservoir AS to the culture vessel RC1. The emptying of the sterilizing solution is done by the valve Va1. A cleaning solution is then applied from the cleaning solution reservoir AC to the culture vessel RC1. The emptying of the cleaning solution is done by the valve Va1. A rinsing solution is then applied from the rinsing solution reservoir AR to the culture vessel RC1. The emptying of the rinsing solution is done by valve Va1. These steps are not represented.

According to FIG. 1*c*, part of the suspension in culture vessel RC2 is transferred to culture vessel RC1, as shown by arrow f21. Leveling valve Vt2 and supply valves Va1 and 2 are in the active position (in black in FIG. 1*c*) and therefore open, so that part of the suspension from the second vessel RC2 passes through said valves to the first culture vessel RC1. The discharge valve Vd2 of the second vessel is in the active position (in black in FIG. 1*c*) and therefore closed, so as to allow the pressurization of RC2 and allow the transfer of half of the suspension to RC1. Discharge valve Vd1 of the first vessel remains in the inactive and thus open position, so as to allow filling into the first culture vessel RC1. In order to allow culture vessel RC2 to be emptied, gas supply device G2 injects a pressurized gas stream, known as the transfer stream, via the gas supply line CG, which increases the pressure in the second culture vessel RC2 and thus pushes the suspension like a syringe plunger via the transfer line.

In a manner not illustrated, a pressurized gas stream is injected into both culture vessels RC1 and RC2 respectively, via the gas supply device G1 and G2, allowing gas to be injected into the suspension and homogenization of the suspension (bubbling agitation) inside culture vessels RC1 and RC2.

According to FIG. 1*b*, all of the suspension in culture vessel RC3 is transferred to culture vessel RC1, as suggested by arrow f31. Supply valves Va3, 3, 2, Va1 are in the active position and therefore open, so that the suspension from the first vessel RC3 passes through said valves to the second culture vessel RC1. Discharge valve Vd3 of the third vessel is in the active position and thus closed, so as to pressurize the third culture vessel. Discharge valve Vd1 of the first vessel remains in the inactive and thus open position, so as to allow filling into the first culture vessel RC1. In order to allow culture vessel RC3 to be emptied, gas supply device G3 injects a pressurized gas stream, known as the transfer stream, via gas supply line CG, which makes it possible to increase the pressure in culture vessel RC3 and thus pushes the suspension like a syringe plunger. Culture vessel RC1 then becomes the mixing vessel and comprises both the suspension initially contained in the first culture vessel RC1 and the suspension from the third culture vessel RC3.

In a manner not illustrated, a pressurized gas stream is injected into the first culture vessel RC1 allowing gas to be injected, via gas supply device G1, into the suspension and the homogenization of the suspension (bubbling agitation) inside culture vessel RC1.

Regarding the second culture vessel RC2, the culture step is maintained by injecting pressurized gas stream into culture vessel RC2 and by keeping valve Vd2 open.

Regarding culture vessel RC3, the sterilization, cleaning and rinsing steps are carried out by opening valves 1, 2, 3, and Va3. First, the sterilization step is started by adding a sterilizing solution from the sterilizing solution reservoir AS to culture vessel RC3. The emptying of the sterilizing solution is done by valve Va3. A cleaning solution is then applied from the cleaning solution reservoir AC to culture vessel RC3. The emptying of the cleaning solution is done by valve Va3. A rinsing solution is then applied from the rinsing solution reservoir AR to culture vessel RC3. The emptying of the rinsing solution is done by valve Va3. These steps are not represented.

According to FIG. 1*c*, part of the suspension in culture vessel RC1 is transferred to culture vessel RC3, as suggested by arrow f13. Leveling valve Vt1 and supply valves 2, 3 and Va3 are in the active position and therefore open, so that part of the suspension from the first vessel RC1 passes through said valves to reach the third culture vessel RC3. Discharge valve Vd1 of the first vessel is in the active position and therefore closed, so as to allow the pressurization of RC1 and allow the transfer of half of the suspension to RC3. Discharge valve Vd3 of the third vessel remains in the inactive position and thus open, so as to allow the filling of the third culture vessel RC3. In order to allow culture vessel RC1 to be emptied, the gas supply device G1 injects a pressurized gas stream, known as the transfer stream, via the gas supply line CG, which increases the pressure in the first culture vessel RC1 and thus pushes the suspension like a syringe plunger via the transfer line.

In a manner not illustrated, a pressurized gas stream is injected into both culture vessels RC1 and RC3 respectively, allowing gas to be injected, via the gas supply device G1 and G3, into the suspension and homogenization of the cell suspension (bubbling agitation) inside culture vessels RC1 and RC3.

According to FIG. 1*b*, all of the suspension in culture vessel RC2 is transferred to culture vessel RC3, as suggested by arrow f23. Supply valves Va2, 3, Va3 are in the active position and therefore open, so that the suspension from the second vessel RC2 passes through said valves to the third culture vessel RC3. Discharge valve Vd2 of the second vessel is in the active position and thus closed, so as to pressurize the second culture vessel. Discharge valve Vd3 of the third vessel remains in the inactive position and thus open, so as to allow filling into the third culture vessel RC3. In order to allow culture vessel RC1 to be emptied, the gas supply device G1 injects a pressurized gas stream, known as the transfer stream, via the gas supply line CG, which makes it possible to increase the pressure in culture vessel RC1 and thus pushes the suspension like a syringe plunger. Culture vessel RC3 then becomes the mixing vessel and comprises both the suspension initially contained in the third culture vessel RC3 and the suspension from the second culture vessel RC2.

In a manner not illustrated, a pressurized gas stream is injected into the second culture vessel RC3 allowing, via the gas supply device G3, the gas injection of the suspension and the homogenization of the cell suspension (bubbling agitation) inside culture vessel RC3.

Regarding the first culture vessel RC1, the culture step is maintained by injecting pressurized gas stream into culture vessel RC1 and by keeping valve Vd1 open.

Regarding culture vessel RC2, the sterilization, cleaning and rinsing steps are carried out by opening valves 1, 2, and Va2. First, the sterilization step is started by adding a sterilizing solution from the sterilizing solution reservoir AS to culture vessel RC2. The emptying of the sterilizing solution is done by valve Va2. A cleaning solution is then applied from the cleaning solution reservoir AC to culture vessel RC2. The emptying of the cleaning solution is done by valve Va2. A rinsing solution is then applied from the rinsing solution reservoir AR to culture vessel RC2. The emptying of the rinsing solution is done by valve Va2. These steps are not represented.

According to FIG. 1*c*, part of the suspension in culture vessel RC3 is transferred to culture vessel RC2, as suggested by arrow f32. Leveling valve Vt3 and supply valves Va2 and 3 are in the active position and therefore open, so that part of the suspension from the third vessel RC3 passes through said valves to reach the second culture vessel RC2. Discharge valve Vd3 of the third vessel is in the active position and therefore closed, so as to allow the pressurization of RC3 and allow the transfer of half of the suspension to RC2. Discharge valve Vd2 of the second vessel remains in the inactive and thus open position, so as to allow the filling of the second culture vessel RC2. In order to allow culture vessel RC3 to be emptied, the gas supply device G3 injects a pressurized gas stream, known as the transfer stream, via the gas supply line CG, which increases the pressure in the third culture vessel RC3 and thus pushes the suspension like a syringe plunger via the transfer line.

In a manner not illustrated, a pressurized gas stream is injected into both culture vessels RC2 and RC3 respectively, via the gas supply device G2 and G3, allowing gas to be injected into the suspension and homogenization of the cell suspension (bubbling agitation) inside culture vessels RC2 and RC3.

A pressurized gas stream is again injected into each of the three culture vessels via the gas supply device G1, G2 or G3 respectively, allowing the injection of gas into the suspension and the homogenization of the cell suspension (bubbling agitation) inside each of the three culture vessels. Supply valves 1, 2, 3, leveling valves Vt1, Vt2 and Vt3, and supply valves Va1, Va2 and Va3 are in the closed position. Only discharge valves Vd1, Vd2 and Vd3 are in the open position.

The preceding steps are repeated as many times as necessary until cells having a phenotype of interest are obtained in the culture vessels.

When the cells have acquired a phenotype of interest, the collection step is performed; this step is not shown. The collection step can also be performed after several mixing cycles. Preferably, the collection step is performed using a harvesting means, in particular by syringe 11.

Once the collection step has been carried out, all the culture vessels are emptied, by closing discharge valves Vd1, Vd2 and Vd3, injecting pressurized gas stream from the external gas source GS, and opening supply valves Va1, va2, Va3 and 2, 3. The sterilization, cleaning, and rinsing steps are then carried out by opening valves 1, Va1, Vd1, 2, Va2, Vd2, 3, Va3, Vd3. First, the sterilization step is started by adding a sterilizing solution from the sterilizing solution reservoir AS to each of culture vessels RC1, RC2, and RC3. The emptying of the sterilizing solution is carried out by the respective valves Va1, Va2 and Va3. A cleaning solution is then applied from the cleaning solution reservoir AC to each of culture vessels RC1, RC2, and RC3. The emptying of the cleaning solution is carried out by the respective valves Va1, Va2 and Va3. A rinsing solution is then applied from the rinsing solution reservoir AR to each of culture vessels RC1, RC2, and RC3. The emptying of the rinsing solution is carried out by the respective valves Va1, Va2 and Va3. These steps are not shown in FIGS. 1*a*, 1*b* and 1*c*.

FIGS. 2*a*, 2*b* and 2*c* represent a second particular embodiment wherein the culture device comprises a single mixing vessel, independent of the culture vessels, and is arranged to receive the contents of all the culture vessels.

The culture device of FIG. 2*a* will be described only in terms of its differences from the culture device in FIG. 1*a*. The culture device of FIG. 2*a* further comprises a single mixing vessel RM, independent of culture vessels RC1, RC2 and RC3, and arranged to receive the contents of said culture vessels. The culture device comprises a gas supply device GM connected to the mixing vessel RM at the top of said mixing vessel. The gas supply device GM allows the mixing vessel to be pressurized by injecting a gas stream. The device includes a gas supply valve Vgm controlling the gas supply to the gas supply device GM. The culture device comprises a discharge device Wm connected to the mixing vessel RM in the upper part of said mixing vessel. The discharge device (Wm) allows the evacuation of gases during mixing. The device comprises a discharge valve Vdm controlling the discharge of gases during mixing. The discharge valve Vdm is normally in the closed position in the inactive state. When the discharge valve Vdm is in the open position, the filling of the mixing vessel and/or evacuation of gases during mixing can be carried out. The culture device comprises a supply valve Vam controlling the filling and emptying of the mixing vessel. It is located in the lower part of the mixing vessel and is connected to the main supply line C10, allowing the filling of the mixing vessel when transferring all or part of the suspension from the culture vessels to the mixing vessel and allowing the emptying of the mixing vessel when transferring all or part of the suspension from the mixing vessel to a culture vessel. The supply valve Vam is normally in the closed position in the inactive state. When the supply valve Vam is in the open position, the mixing vessel can be filled or emptied. When the supply valve Vam is in the closed position, it is not possible to fill or empty the mixing vessel.

The method for continuous cell culture of living cells associated with the culture device shown in FIGS. 2*a*, 2*b* and 2*c* will now be described.

According to FIG. 2*a*, each of the three culture vessels RC1, RC2, and RC3 comprises living cells in a culture medium. They are filled to about 75% of their total capacity. The mixing vessel RM is empty and valves Vdm, Vam and Vgm are in the closed position.

According to FIG. 2*b*, the suspensions contained in culture vessels RC1, RC2 and RC3 are transferred to mixing vessel RM, as represented by arrows f1*m*, f2*m*, f3 *m* and fmp. For this purpose, the transfer of the suspension from culture vessel RC1 to mixing vessel RM is carried out by opening supply valves Va1, 2, 3, Vam and discharge valve Vdm. The transfer of the suspension from culture vessel RC2 to mixing vessel RM is carried out by opening supply valves Va2, 3, Vam and discharge valve Vdm. The transfer of the suspension from culture vessel RC3 to mixing vessel RM is carried out by opening supply valves Va3, Vam and discharge valve Vdm. Opening discharge valve Vdm allows the mixing vessel RM to be filled. The transfer of the suspensions is achieved by means of gas supply devices G1, G2 and G3, as described above.

Once the mixing vessel has been filled with all the suspensions from culture vessels RC1, RC2 and RC3, supply valve Vam is placed in the closed position.

Regarding culture vessels RC1, RC2 and RC3, the sterilization, cleaning and rinsing steps are carried out by opening valves 1, Va1, Vd1, 2, Va2, Vd2, 3, Va3, Vd3. First, the sterilization step is started by adding a sterilizing solution from the sterilizing solution reservoir AS to each of culture vessels R1C, RC2, and RC3. The emptying of the sterilizing solution is carried out by the respective valves Va1, Va2 and Va3. A cleaning solution is then applied from the cleaning solution reservoir AC to each of culture vessels RC1, RC2, and RC3. The emptying of the cleaning solution is carried out by the respective valves Va1, Va2 and Va3. A rinsing solution is then applied from the rinsing solution reservoir AR to each of culture vessels RC1, RC2, and RC3. The emptying of the rinsing solution is carried out by the respective valves Va1, Va2 and Va3. These steps are not shown in FIG. 2*b*.

According to FIG. 2*c*, part of the suspension in mixing vessel RM is transferred to culture vessel RC1, as shown by arrows fms and fm1. For this purpose, the transfer is made by opening valves Vgm, Vam, 3, 2, Va1 and Vd1. Valve Vdm is in the closed position and a pressurized gas stream is injected into mixing vessel Rm, via the opening of gas supply valve Vgm, allowing mixing vessel RM to be emptied. Opening discharge valve Vd1 allows culture vessel RC1 to be filled. Valves Va2 and Va3 are in the closed position.

As suggested by FIG. 2*c*, a portion of the suspension in mixing vessel RM is then transferred to the second culture vessel RC2, as represented by dashed arrows fms and fm2. For this purpose, the transfer is made by opening valves Vgm, Vam, 3, Va2 and Vd2. Valve Vdm is in the closed position and a pressurized gas stream is injected into mixing vessel Rm, via the opening of gas supply valve Vgm, allowing mixing vessel RM to be emptied. Opening discharge valve Vd2 allows culture vessel RC2 to be filled. Valves Va1 and Va3 are in the closed position.

As suggested by FIG. 2*c*, a portion of the suspension in mixing vessel RM is then transferred to the third culture vessel RC3, as represented by dashed arrows fms and fm3. For this purpose, the transfer is made by opening valves Vgm, Vam, Va3, and Vd3. Valve Vdm is in the closed position and a pressurized gas stream is injected into mixing vessel Rm, via the opening of gas supply valve Vgm, allowing mixing vessel RM to be emptied. Opening discharge valve Vd3 allows culture vessel RC3 to be filled. Valves Va1 and Va2 are in the closed position.

Once the transfer has been completed and the mixing vessel has been totally emptied, the sterilization, cleaning and rinsing steps are carried out by opening valves 1, 2, 3, Vam and Vdm. First, the sterilization step is started by adding a sterilizing solution from the sterilizing solution reservoir AS to the culture vessel RM. The emptying of the sterilizing solution is done by valve Vam. A cleaning solution is then applied from the cleaning solution reservoir AC to mixing vessel RM. The emptying of the cleaning solution is done by valve Vam. A rinsing solution is then applied from the rinsing solution reservoir AR to the mixing vessel RM. The emptying of the rinsing solution is done by valve Vam. These steps are not shown in FIGS. 2*a* to 2*c*.

A pressurized gas stream is again injected into each of the three culture vessels RC1, RC2 and RC3 via the gas supply device G1, G2 or G3 respectively, allowing the injection of gas and the homogenization of the suspension (bubbling agitation) inside each of the three culture vessels. Supply valves 1, 2, 3, leveling valves Vt1, Vt2 and Vt3, and supply valves Va1, Va2 and Va3 are in the closed position. Only discharge valves Vd1, Vd2 and Vd3 are in the open position.

The collection step, after several culture cycles of the living cells that have acquired a phenotype of interest in the culture vessels, is then performed, this step not being shown.

Once the collection step has been completed, all of the culture vessels are emptied in the same manner as in the first embodiment. These steps are not shown in FIGS. 2*a* to 2*c*.

The culture device of FIG. 3 will be described only in terms of its differences from the culture device in FIG. 1*a*.

The device for continuous cell culture of living cells, as shown in FIG. 3, comprises four culture vessels, a first culture vessel RC1, a second culture vessel RC2, a third culture vessel RC3 and a fourth vessel RC4. In this embodiment, the set of culture vessels is arranged to respectively and successively become a mixing vessel during the cell culture method, each mixing vessel being arranged to receive the contents of at least two culture vessels. Each of culture vessels RC1, RC2, RC3, and RC4 is connected individually, and independently of each other, to a sterile fluid supply unit 10 described above. The sterile fluid supply unit (10) is connected to its culture vessel via a supply valve 1.

According to FIG. 3, each of the four culture vessels comprises living cells in a culture medium. The living cells are put in culture to obtain a suspension. For this purpose, a pressurized gas stream is injected into each of the four culture vessels via the gas supply device G1, G2, G3, or G4 respectively, allowing the injection of gas and the homogenization of the suspension (bubbling agitation) inside each of the four culture vessels RC1, RC2, RC3 and RC4. The supply valves 1, leveling valves Vt1, Vt2, Vt3, and Vt4, and supply valves Va1, Va2, Va3, and Va4 are in the closed position. Only discharge valves Vd1, Vd2, Vd3, and Vd4 are in the open position.

The culture device comprises valves V10, V20, V30, and V40 allowing the interconnection of the four culture vessels, and are normally in the closed position in the inactive state.

The method of continuous cell culture of living cells associated with the culture device shown in FIG. 3 is similar to the culture method associated with FIGS. 1*a*, 1*b* and 1*c*.

First, all of the suspension in the first culture vessel RC1 is transferred to culture vessel RC2, as suggested by arrow f12. For this purpose, the transfer is made by opening valves Va1, V10, V20, Va2, and Vd2. Valve Vd1 is in the closed position, allowing culture vessel RC1 to be emptied by the gas supply device as described above. Opening discharge valve Vd2 allows culture vessel RC2 to be filled. Culture vessel RC2 then becomes the mixing vessel and comprises both the suspension initially contained in culture vessel RC2 and the suspension from culture vessel RC1. A pressurized gas stream is injected into culture vessel RC2 allowing, via gas supply device G2, the gas injection of the suspension and the homogenization of the cell suspension (bubbling agitation) inside culture vessel RC2. In culture vessels RC3 and RC4, the culture step is maintained by injecting pressurized gas stream into culture vessel RC3 and RC4 and by keeping valves Vd3 and Vd4 open.

In culture vessel RC1, the sterilization, cleaning and rinsing steps are then carried out by opening valves 1, Va1, Vd1. First, the sterilization step is started by adding a sterilizing solution from the sterilizing solution reservoir AS to culture vessel RC1. The emptying of the sterilizing solution is done by valve Va1. A cleaning solution is then applied from the cleaning solution reservoir AC to culture vessel RC1. The emptying of the cleaning solution is done by valve Va1. A rinsing solution is then applied from the rinsing solution reservoir AR to culture vessel RC1. The emptying of the rinsing solution is done by valve Va1. These steps are not shown in FIG. 3.

Next, part of the suspension in culture vessel RC2 is transferred to culture vessel RC1, as shown by arrow f21. For this purpose, the transfer is made by opening valves Vt2, V20, V10, Va1, and Vd1. Valve Vd2 is in the closed position, allowing the emptying of culture vessel RC2 by applying pressure on the suspension using the gas injected by GC2. Opening discharge valve Vd1 allows culture vessel RC1 to be filled. A pressurized gas stream is injected into both culture vessels RC1 and RC2 respectively, allowing gas to be injected, via the gas supply device G1 and G2, into the suspension and homogenization of the cell suspension (bubbling agitation) inside culture vessels RC1 and RC2. In the third culture vessels RC3 and RC4, the culture step is maintained by injecting pressurized gas stream into culture vessels RC3 and RC4 and by keeping valves Vd3 and Vd4 open.

Then, the entire suspension in culture vessel RC3 is transferred to the first culture vessel RC1, as suggested by dotted arrow f13. For this purpose, the transfer is made by opening valves Va1, V10, V30, Va3 and closing valve Vd3. Then, the sterilization, cleaning, and rinsing of vessel RC3 is performed as described above for vessel RC1. Next, after mixing, part of the suspension in culture vessel RC1 is transferred to culture vessel RC3, as shown by arrow f31. For this purpose, the transfer is made by opening valves Vt1, V30, V10, Va1 and closing valve Vd1.

The entire suspension in culture vessel RC1 is transferred to the first culture vessel RC4, as suggested by dotted arrow f14. For this purpose, the transfer is made by opening valves Va1, V10, V40, Va4 and closing valve Vd1. Next, after mixing, part of the suspension in culture vessel RC4 is transferred to culture vessel RC1, as shown by arrow f41. For this purpose, the transfer is made by opening valves Vt4, V40, V10, Va1 and closing valve Vd4.

Then, the entire suspension in culture vessel RC2 is transferred to the third culture vessel RC3, as suggested by dotted arrow f23. For this purpose, the transfer is made by opening valves Va2, V20, V30, Va3 and closing valve Vd2. Then, the sterilization, cleaning, and rinsing of vessel RC2 is performed as described above for vessel RC1. Next, after mixing, part of the suspension in culture vessel RC3 is transferred to culture vessel RC2, as suggested by arrow f32. For this purpose, the transfer is made by opening valves Vt3, V30, V20, Va2 and closing valve Vd3.

The entire suspension in culture vessel RC4 is transferred to the first culture vessel RC2, as suggested by dotted arrow f24. For this purpose, the transfer is made by opening valves Va2, V20, V40, Va4 and closing valve Vd4. Then, the sterilization, cleaning, and rinsing of vessel RC4 is performed as described above for vessel RC1. Next, after mixing, part of the suspension in culture vessel RC2 is transferred to culture vessel RC4, as suggested by dotted arrow f42. For this purpose, the transfer is made by opening valves Vt4, V40, V20, Va2 and closing valve Vd2.

Lastly, the entire suspension in culture vessel RC3 is transferred to the first culture vessel RC4, as suggested by dotted arrow f34. For this purpose, the transfer is made by opening valves Va3, V30, V40, Va4 and closing valve Vd3. Next, after mixing, part of the suspension in culture vessel RC4 is transferred to the third culture vessel RC3, as suggested by dotted arrow f43. For this purpose, the transfer is made by opening valves Vt4, V40, V30, Va3 and closing valve Vd4.

The culture device of FIG. 4 will be described only in terms of its differences from the culture device in FIG. 3.

FIG. 4 represents a fourth particular embodiment comprising four culture vessels and a single mixing vessel RM, independent of the set of culture vessels, and which is arranged to receive the contents of the set of culture vessels RC1, RC2, RC3 and RC4. Each of culture vessels RC1, RC2, RC3, and RC4 is connected individually, and independently of each other, to a sterile fluid supply unit 10 described above. The sterile fluid supply unit (10) is connected to its culture vessel via a supply valve 1.

The method of continuous cell culture of living cells associated with the culture device shown in FIG. 4 is similar to the culture method associated with FIGS. 2*a*, 2*b*, and 2*c*.

Advantageously, the suspensions contained in culture vessels RC1, RC2, RC3 and RC4 are transferred to the mixing vessel RM.

The sterilization, cleaning, and rinsing operations of vessels RC1, RC2, RC3 and RC4 are then applied.

Once the mixing step is completed, part of the suspension contained in the mixing vessel RM is then transferred to the first culture vessel RC1. Part of the suspension in the mixing vessel RM is then transferred to the second culture vessel RC2. Part of the suspension in the mixing vessel RM is then transferred to the third culture vessel RC3. Part of the suspension in the mixing vessel RM is then transferred to the fourth culture vessel RC4.

Next, the operations of sterilization, cleaning and rinsing of the mixing vessel RM are applied.

EXAMPLES

In all the examples described hereafter, the growth regime is that of the turbidostat for which the dilution rate (in hours$^{-1}$) is defined as the ratio between the flow rate of growth medium, to maintain a constant concentration of microorganisms in the culture chamber during the evolution, and the volume of the culture chamber. In these experiments, the turbidostat was implemented such that the dilution rate was equivalent to the population growth rate.

Example 1: Evolutionary Adaptation of a Bacterial Strain to a Temperature of 30° C.

At a suboptimal temperature, that is below the optimal temperature, the growth rate of an organism is lower than at the optimal temperature. When the organism is intended for use in a context where the temperature is lower than the optimal temperature, it is relevant to adapt this organism to said temperature.

In experiments 1 and 2 described below, the strain used is a soil bacterium of the family Pseudomonadaceae. The specific growth rate of this strain on synthetic growth medium containing 20 g/L sucrose as a carbon source is 0.315 h$^{-1}$ at the optimum temperature of 35° C.

For each of the two experiments, the objective is to adapt this strain to a temperature of 30° C., with the aim of achieving a growth rate at 30° C. comparable to that of the starting strain at 35° C.

To achieve this objective, two adaptive evolution experiments were conducted using the same strain described above, in the same setup and using the same reference medium described above.

1/ Experiment 1: Comparative Method not Part of the Invention: Turbidostat at the Target Temperature of 30° C.

Experiment 1 consisted of the evolutionary adaptation of the aforementioned bacterium according to a simple evolutionary protocol not in accordance with the present invention, implementing only the turbidostat selective regime in a single culture vessel.

At the beginning of the experiment, the culture vessel is inoculated with the strain described above.

During the experiment, the temperature is kept fixed and equal to 30° C.

The selective regime is implemented in a discontinuous way as follows: every ten minutes, the transparency measured by optical measurement is compared to a threshold arbitrarily set at 80:

- If the measured value is above the threshold, no action is triggered,
- If the measured value is below the threshold, a dilution of the suspension is performed by adding a volume of 4 mL of the growth medium described above in the culture vessel, keeping the volume of the suspension constant at 13.5 mL in the culture vessel, withdrawing the same volume V of suspension present in the culture vessel.

Results Obtained:

The results obtained are presented in FIG. 5.

The number of 29 daily dilutions, equivalent to a theoretical dilution rate or growth rate of 0.358 h$^{-1}$, is reached after 20 days of adaptive evolution in turbidostat at 30° C.

2/ Experiment 2: Method According to the Invention Using Two Culture Vessels Experiment 2 consisted of the evolutionary adaptation of the same bacterium mentioned above according to the method of the invention and implementing two culture vessels RC1 and RC2 at distinct temperatures. This protocol is implemented in the same device as the one used for experiment 1.

At the beginning of the experiment, each culture vessel RC1 and RC2 is inoculated with the same strain described above that was used for inoculation at the beginning of experiment 1 and the initial temperature is 35° C. in both RC1 and RC2.

In each of the two culture vessels RC1 and RC2, the selective regime is the turbidostat, implemented in a discontinuous manner as described in experiment 1, with the same parameters as used in experiment 1:

- Growth medium as defined above
- Transparency threshold=80,
- Dilution of the suspension by adding a volume of 4 mL of the growth medium in the culture vessel, keeping the volume of the suspension constant at 13.5 mL in the culture vessel, withdrawing the same volume V of suspension present in the culture vessel.

The growth stage is defined by a duration arbitrarily set at 12 hours, at the end of which step c) is carried out by transferring the entire contents of the culture vessel RC1 to the culture vessel RC2, which becomes the mixing vessel. Each cycle therefore has a duration of 12 hours and there are two cycles per day.

At each new cycle, the temperature in each of these two culture vessels RC1 and RC2 is automatically adjusted according to the calculation of the average dilution rate in vessel RC1, with the instruction to decrease the culture temperature as soon as the dilution rate in vessel RC1, averaged over the cycle just completed, is greater than a threshold arbitrarily set at the value of 0.358 h$^{-1}$ obtained during experiment 1 after 20 days in a turbidostat at 30° C.

Table 1 below lists the temperatures applied in each of the two culture vessels RC1 and RC2 during successive cycles, taking into account that only one cycle took place on day 7 of the experiment.

TABLE 1

| Duration of the experiment (days) | Cycle | Temperature of Vessel 1 (° C.) at the start of the cycle | Temperature of Vessel 2 (° C.) at the start of the cycle |
|---|---|---|---|
| 1 | 1 | 35 | 35 |
| 1 | 2 | 34.9 | 34.8 |
| 2 | 3 | 34.9 | 34.8 |
| 2 | 4 | 34.8 | 34.9 |
| 3 | 5 | 34.6 | 34.8 |
| 3 | 6 | 34.4 | 34.6 |
| 4 | 7 | 34.1 | 34.4 |
| 4 | 8 | 33.7 | 34.1 |
| 5 | 9 | 33.3 | 33.7 |
| 5 | 10 | 32.5 | 33.3 |
| 6 | 11 | 31.7 | 32.5 |
| 6 | 12 | 30.1 | 31.7 |
| 7 | 13 | 28.5 | 30.1 |
| 8 | 14 | 28.5 | 30.1 |
| 8 | 15 | 29.3 | 30.1 |
| 9 | 16 | 29.7 | 30.1 |
| 9 | 17 | 29.9 | 30.1 |
| 10 | 18 | 30 | 30.1 |
| 10 | 19 | 29.9 | 30 |
| 11 | 20 | 29.8 | 29.9 |
| 11 | 21 | 29.6 | 29.8 |

Results Obtained:

The results obtained are presented in FIGS. 6 and 7.

During the 18th culture cycle, i.e. after 10 days of adaptive evolution, the temperature in culture vessel RC1 is 30° C. During this cycle, the average dilution rate is 0.387 $h^{-1}$, higher than the average dilution rate obtained after 20 days of adaptive evolution in turbidostat at 30° C. in the same device.

To compare growth rates, it is legitimate to compare the dilution rate over one cycle of experiment 2 to that measured in experiment 1 because, during each cycle, the suspension is exposed to the turbidostat selective regime implemented according to the same batch protocol, with the same parameters and in the same device (culture vessel RC1 in experiment 2 being precisely the same culture vessel as the one used in experiment 1).

Thus, it can be stated that the suspension grown in the 18th cycle, on day 10 of Experiment 2, displays a slightly higher growth rate at 30° C. than that obtained on day 20 of turbidostat Experiment 1 at 30° C.

Conclusion

Therefore, the protocol in Experiment 2, which implements parallel evolutionary adaptation of two subpopulations that are regularly mixed and redistributed into the two culture vessels according to the method of the invention, made it possible to adapt a bacterium to a suboptimal temperature twice as fast as with a conventional turbidostat regime where a single population is grown in a single vessel.

Example 2: Evolutionary Adaptation of a Bacterial Strain to a Temperature of 25° C.

For both experiments, the objective is to adapt this strain to a temperature of 25° C. while increasing the growth rate.

To achieve this objective, two adaptive evolution experiments were conducted using the same strain as used in Example 1, initially evolved at 35° C. with a dilution rate of 0.315 $hours^{-1}$, within the same setup and using the same reference medium.

1/ Experiment 3: Comparative Method not Part of the Invention: Turbidostat at the Target Temperature of 25° C.

This experiment was carried out under the same conditions as shown above in Example 1 for Experiment 1/but at a temperature of 25° C.

Experiments were performed with single culture vessels of either 15 mL or 80 mL volume.

Results Obtained:

The results are shown in the attached FIG. 8. In this figure the dilution rate ($hours^{-1}$) is a function of the number of days. The curve with the solid circles corresponds to the experiment performed in the 80 mL vessel and the curve with the solid squares corresponds to the experiment performed in the 15 mL vessel.

It is observed that the dilution rate or growth rate of 0.2 $hours^{-1}$ at 25° C. is obtained in 18 days in both the 15 mL volume culture vessel and the 80 mL volume vessel, indicating that the volume of the culture vessel is not a critical parameter for the evolution of microorganisms.

2/ Experiment 4: Method According to the Invention Using Two Culture Vessels with a Prescribed Dilution Rate of 0.2 $Hours^{-1}$ Experiment 4 consisted of the evolutionary adaptation of the same bacterium according to the method of the invention using two culture vessels RC1 and RC2, each having a volume of 15 mL, according to the protocol described in Experiment 2 of Example 1, but varying the temperature from 35° C. to 25° C.

At the beginning of the experiment, each culture vessel RC1 and RC2 is inoculated with the same strain as in Example 1 and the initial temperature is 35° C. in both vessels RC1 and RC2.

At each new cycle, the temperature in each of these two culture vessels RC1 and RC2 is automatically adjusted according to the calculation of the average dilution rate in the vessel, with the instruction to decrease the culture temperature as soon as the dilution rate in culture vessel RC1, averaged over the cycle just completed, is greater than a threshold arbitrarily set at the value of 0.2 $hours^{-1}$, value obtained during Experiment 3 after 18 days in a turbidostat at 25° C.

Table 2 below lists the temperatures applied in each of the two culture vessels RC1 and RC2 during successive cycles.

TABLE 2

| Duration of the experiment (days) | Cycle | Temperature of Vessel 1 (° C.) at the start of the cycle | Temperature of Vessel 2 (° C.) at the start of the cycle |
|---|---|---|---|
| 0.0 | 1 | 35 | 35 |
| 0.5 | 2 | 34.9 | 34.6 |
| 1.0 | 3 | 34.6 | 34.4 |
| 1.5 | 4 | 34.4 | 34 |
| 2.0 | 5 | 34.4 | 34 |
| 2.5 | 6 | 34 | 33.6 |
| 3.0 | 7 | 33.6 | 32.8 |
| 3.5 | 8 | 32.8 | 31.9 |
| 4.0 | 9 | 31.9 | 30.9 |
| 4.5 | 10 | 30.9 | 29.9 |

TABLE 2-continued

| Duration of the experiment (days) | Cycle | Temperature of Vessel 1 (° C.) at the start of the cycle | Temperature of Vessel 2 (° C.) at the start of the cycle |
|---|---|---|---|
| 5.0 | 11 | 29.9 | 28.9 |
| 5.5 | 12 | 28.9 | 27.9 |
| 6.0 | 13 | 27.9 | 26.9 |
| 6.5 | 14 | 26.9 | 25.9 |
| 7.0 | 15 | 25.9 | 24.9 |

The results obtained are shown in the attached FIG. 9.

In this figure the temperature (° C.) is a function of the number of days. The curve with the solid diamonds corresponds to the experiment performed in vessel RC1 and the curve with the solid squares corresponds to the experiment performed in vessel RC2.

These results show that the adaptation of the bacteria at 25° C. for a dilution rate or growth rate of 0.2 hours$^{-1}$ is obtained in 7 days according to the method of the invention implementing the repeated mixing of the contents of 2 culture vessels, i.e. 2.6 times faster than according to the method of Experiment 3/not in accordance with the invention.

The benefit observed on the evolutionary adaptation method is indeed caused by the method according to the invention consisting of periodically combining and separating the suspensions coming from at least two culture vessels.

The invention claimed is:

1. A method for adaptive evolution of living cells, excluding human embryonic stem cells, by continuously culturing said living cells, wherein n culture vessels (RCi) are used, i ranging from 1 to n, where n≥2, said method comprising:

a) introducing at least one liquid culture medium and living cells into each of the n culture vessels (RCi);

b) in each of the n culture vessels (RCi), culturing said living cells according to a given selective regime, using predefined culture parameters, until a determined growth stage is reached in at least one of the n culture vessels (RCi), so as to obtain, in each of the n culture vessels (RCi), a suspension of living cells in said liquid culture medium;

c) transferring:

at least a portion of the suspension of living cells obtained in step b) from at least two of the n culture vessels (RCi) to at least n−1 mixing vessels (RMj), j ranging from 1 to n−1, so as to perform a destination transfer, or at least a portion of the suspension of living cells obtained in step b) from at least one of the n culture vessels (RCi) to a different one of the n culture vessels (RCi) so as to perform a destination transfer;

d) homogenizing the transferred suspensions of the destination transfer of step c) to obtain a homogenized suspension of mixed living cells;

e) transferring at least a portion of the homogenized suspension obtained in step d) into at least two of the n culture vessels (RCi) so as to perform a return transfer;

f) repeating the preceding steps b) to e) at least once by varying RCi and RMj so that each of the at least two of the n culture vessels (RCi) is mixed at least twice; and g) collecting after step f) living cells that have acquired a phenotype of interest from at least one of the n culture vessels (RCi).

2. The method according to claim 1, wherein the living cells are eukaryotic cells or prokaryotic cells.

3. The method according to claim 1, wherein the selective regime of step b) comprises chemostat conditions, turbidostat conditions, medium swap, or iterated batch.

4. The method according to claim 1, wherein the predefined culture parameters of step b) comprise temperature, pH, cell density, culture medium composition, gas composition, exposure to electromagnetic radiation of a particular wavelength, exposure to a mutagenic agent, or a combination thereof.

5. The method according to claim 1, wherein the destination transfer of step c) is carried out by transferring at least a portion of the suspension of living cells obtained in step b) from at least two of the n culture vessels (RCi) to the at least n−1 mixing vessels (RMj).

6. The method according to claim 1, wherein step c) is carried out by transferring at least a portion of the suspension of living cells obtained in step b) from at least one of the n culture vessels (RCi) to a different one of the n culture vessels (RCi) so as to perform a destination transfer.

7. The method according to claim 1, wherein the homogenizing of the transferred suspensions in step d) comprises agitation.

8. The method according to claim 1, wherein step e) consists of transferring at least a portion of the homogenized suspension of mixed living cells obtained in step d) to at least two culture vessels (RCi).

9. The method according to claim 8, wherein at least a portion of the suspension transferred in step e) corresponds to a fraction between 1 and 100% of the volume of said homogenized suspension of mixed living cells.

10. The method according to claim 1, wherein, when repeating step b), the selective regime and/or the predefined culture parameters used during a culture cycle are the same as those used during the preceding culture cycle.

11. The method according to claim 5, wherein steps c) to f) in combination comprise:

i) transferring at least a portion of the suspension of living cells obtained in step b) from a culture vessel (RCi) to a mixing vessel (RMj), so as to perform a destination transfer;

ii) homogenizing the suspension transferred from the culture vessel (RCi) to the mixing vessel (RMj), to obtain a homogenized suspension of mixed living cells;

iii) transferring at least part of the homogenized suspension obtained in step ii) from the mixing vessel (RMj) to the culture vessel (RCi) from which transfer was made in step i), so as to perform a return transfer, wherein part of the homogenized suspension that is not transferred remains in the mixing vessel (RMj) for any subsequent homogenizing step ii);

iv) repeating the preceding steps i) to iii) n−(i+1) times while incrementing i by one unit at each repetition so as to transfer all or part of the suspension from the culture vessel (RCi) to a mixing vessel RMj+1 so as to perform n−(i+1) further destination transfers and n−(i+1) further return transfers;

v) repeating steps i) to iv) n−(i+1) times while incrementing i by one at each repetition so that the culture vessel becomes RCi+1 after each end of step iv).

12. The method according to claim 5, wherein each of said at least n−1 mixing vessel (RMj) is independent of the at least two n culture vessels (RCi) and is arranged to receive the contents of the n culture vessels.

13. The method according to claim 12, wherein steps c) to e) are carried out as follows:

c) transferring at least a portion of the suspension of living cells obtained in step b) from at least two culture vessels (RCi) to the at least one of said n−1 mixing vessel (RMj) to obtain a suspension of mixed living cells;

d) homogenizing the mixed suspension of living cells obtained in step c) in the at least one of said n−1 mixing vessel (RMj), to obtain a homogenized suspension of mixed living cells; and e) transferring at least a portion of the suspension obtained in step d) from the at least one of said n−1 mixing vessel (RMj) to each of the at least two culture vessels (RCi).

14. The method according to claim 1, wherein the living cells are human cells, animal cells, or plant cells.

15. The method according to claim 5, wherein at least one mixing vessel is independent of the at least two culture vessels.

16. The method according to claim 7, wherein the agitation is performed using a mechanical agitator or an injection of a gas stream.

17. The method according to claim 1, wherein, when repeating step b), the selective regime and/or the predefined culture parameter used during a culture cycle are different from those used during the preceding culture cycle.

18. The method of claim 1, wherein the selective regime of step b) comprises chemostat conditions, turbidostat conditions, medium swap, or iterated batch, and wherein the predefined culture parameters of step b) comprise temperature, pH, cell density, culture medium composition, gas composition, exposure to electromagnetic radiation of a particular wavelength, exposure to a mutagenic agent, or a combination thereof.

19. The method of claim 5, wherein the selective regime of step b) comprises chemostat conditions, turbidostat conditions, medium swap, or iterated batch, and wherein the predefined culture parameters of step b) comprise temperature, pH, cell density, culture medium composition, gas composition, exposure to electromagnetic radiation of a particular wavelength, exposure to a mutagenic agent, or a combination thereof.

20. The method of claim 11, wherein the selective regime of step b) comprises chemostat conditions, turbidostat conditions, medium swap, or iterated batch, and wherein the predefined culture parameters of step b) comprise temperature, pH, cell density, culture medium composition, gas composition, exposure to electromagnetic radiation of a particular wavelength, exposure to a mutagenic agent, or a combination thereof.

* * * * *